US008597232B2

(12) United States Patent
Lev et al.

(10) Patent No.: US 8,597,232 B2
(45) Date of Patent: Dec. 3, 2013

(54) MEDICAL APPARATUS AND SINGLE USE KIT INCLUDING LINEAR FLOW CONTROL DEVICE FOR USE THEREWITH FOR RECONSTITUTION AND ADMINISTRATION OF LIQUID DRUG DOSAGE

(75) Inventors: Nimrod Lev, Savion (IL); Zvika Zinger, Eschar (IL); Moshe Gilboa, Kfar Saba (IL)

(73) Assignee: MEDIMOP Medical Projects, Ltd., Ra'anana (IL)

( * ) Notice: Subject to any disclaimer, the term of this patent is extended or adjusted under 35 U.S.C. 154(b) by 0 days.

(21) Appl. No.: 13/518,036

(22) PCT Filed: Dec. 22, 2010

(86) PCT No.: PCT/IL2010/001077
§ 371 (c)(1), (2), (4) Date: Jun. 21, 2012

(87) PCT Pub. No.: WO2011/077434
PCT Pub. Date: Jun. 30, 2011

(65) Prior Publication Data

US 2012/0271229 A1 Oct. 25, 2012

(30) Foreign Application Priority Data

Dec. 23, 2009 (IL) .......................................... 202914

(51) Int. Cl.
*A61M 3/02* (2006.01)
*A61M 5/00* (2006.01)

(52) U.S. Cl.
USPC ............... 604/40; 604/35; 604/258; 604/259; 604/131; 604/151

(58) Field of Classification Search
USPC .............. 604/19, 27, 35, 40, 93.01, 258–259, 604/508, 131, 151, 85
See application file for complete search history.

(56) References Cited

U.S. PATENT DOCUMENTS

| | | | |
|---|---|---|---|
| 4,534,758 | A | 8/1985 | Akers et al. |
| 6,162,199 | A | 12/2000 | Geringer |

(Continued)

FOREIGN PATENT DOCUMENTS

| | | | |
|---|---|---|---|
| DE | 4314657 | A1 | 11/1994 |
| WO | 9629113 | A1 | 9/1996 |

(Continued)

OTHER PUBLICATIONS

Office Action issued Jul. 31, 2012 in U.S. Appl. No. 12/598,469.

(Continued)

*Primary Examiner* — Quynh-Nhu H Vu
(74) *Attorney, Agent, or Firm* — Panitch Schwarze Belisario & Nadel LLP

(57) ABSTRACT

Medical apparatus (10) for use with single use kits (100) containing a flow control device (101), a syringe (40), and one or more vials (60A, 608, 60C), for reconstituting a liquid drug dosage and administrating same. The flow control devices (101) include a core member (116) having an inlet port (107) and a flow control member (117) rotatably mounted on the core member (116) and having at least one vial port (112,113, 114) for attachment of a vial and an outlet port (109). Flow control devices (101) are designed to ensure an inlet port (107) is in flow communication with a single port (112,113, 114) at each flow control position of at least two predetermined flow control positions of a flow control member (117) relative to a core member (116). The medical apparatus (10) includes a housing (11) having a syringe support (12) for horizontally supporting a syringe (40) and a flow control device support (13) for horizontally supporting a flow control device (101). The medical apparatus (10) can be designed for either manual operation or automatic operation.

10 Claims, 22 Drawing Sheets

(56) References Cited

U.S. PATENT DOCUMENTS

| | | | | |
|---|---|---|---|---|
| 6,238,372 | B1 | 5/2001 | Zinger et al. | |
| 6,581,648 | B1 | 6/2003 | Zolentroff et al. | |
| 6,699,232 | B2 * | 3/2004 | Hart et al. | 604/523 |
| 6,953,450 | B2 * | 10/2005 | Baldwin et al. | 604/248 |
| 7,500,961 | B2 | 3/2009 | Nemoto | |
| 7,703,483 | B2 | 4/2010 | Hartman et al. | |
| 7,704,236 | B2 * | 4/2010 | Denolly | 604/191 |
| 7,914,499 | B2 | 3/2011 | Gonnelli et al. | |
| 2002/0123737 | A1 * | 9/2002 | Hart et al. | 604/523 |
| 2004/0162515 | A1 * | 8/2004 | Chornenky et al. | 604/19 |
| 2006/0049209 | A1 * | 3/2006 | Baker | 222/252 |
| 2006/0169348 | A1 | 8/2006 | Yigal | |
| 2006/0224105 | A1 | 10/2006 | Thorne et al. | |
| 2010/0087786 | A1 | 4/2010 | Zinger et al. | |

FOREIGN PATENT DOCUMENTS

| | | | |
|---|---|---|---|
| WO | 2006124634 | A1 | 11/2006 |
| WO | 2007079305 | A2 | 7/2007 |
| WO | 2007130809 | A2 | 11/2007 |
| WO | 2008135989 | A1 | 11/2008 |
| WO | 2013001525 | A1 | 1/2013 |

OTHER PUBLICATIONS

Int'l Search Report and Written Opinion issued on May 4, 2011 in Int'l Application No. PCT/IL2010/001077.

International Search Report Issued Aug. 28, 2008 in Int'l Application No. PCT/IL2008/000606.

Notice of Intention to Grant EP Application No. 08738307.1.

International Search Report dated Mar. 30, 2011 in Int'l Application No. PCT/IL2010/000939.

* cited by examiner

FCP20

FCP21

FCP22

FCP23

MEDICAL APPARATUS AND SINGLE USE KIT INCLUDING LINEAR FLOW CONTROL DEVICE FOR USE THEREWITH FOR RECONSTITUTION AND ADMINISTRATION OF LIQUID DRUG DOSAGE

CROSS-REFERENCE TO RELATED APPLICATION

This application is a Section 371 of International Application No. PCT/IL2010/001077, filed Dec. 22, 2010, which was published in the English language on Jun. 30, 2011, under International Publication No. WO 2011/077434 A1, and the disclosure of which is incorporated herein by reference.

FIELD OF THE INVENTION

The invention pertains to reconstitution and administration of liquid drugs.

BACKGROUND OF THE INVENTION

Commonly owned U.S. Pat. No. 6,238,372's FIGS. 11 to 15 illustrate and describe a fluid control device commercially available under the registered trademark MIXJECT® for liquid drug reconstitution and administration purposes. The fluid control device affords convenient reconstitution with a pre-filled syringe and a single medicament containing vial.

However, certain administration regimes require a greater quantity of medicament than contained in a single medicament containing vial thereby requiring a time consuming and cumbersome serial reconstitution of two or more medicament containing vials. Such serial reconstitutions typically also require at least one replacement of a needle for sterilization purposes further complicating reconstitution prior to dosage administration. Some administration regimes require a greater volume of diluent than can be stored in a pre-filled syringe which is particularly applicable in the case of serial reconstitute on two or vials.

SUMMARY OF THE INVENTION

The present invention is directed toward medical apparatus for use with single use kits containing a flow control device, a syringe, and one or more vials, for reconstituting a liquid drug dosage and administrating same. Kits include one or more vials depending on an intended quantity of medicament to be administered to a subject. Some kits may include a syringe pre-filled with diluent for reconstitution purposes. Other kits may include a vial containing diluent for reconstitution purposes particularly in the case that a greater volume of diluents is required than can be stored in a single pre-filled syringe. The medicament containing vials can contain the same or different medicaments. The present invention is suitable for home users for self administration, professional users at outpatient clinics, hospital departments, and the like.

The flow control devices include a core member having an inlet port and a flow control member rotatably mounted on the core member and having at least one vial port for attachment of a vial and an outlet port. Flow control devices are designed to ensure an inlet port is in flow communication with a single port of the at least one vial port and the outlet port at each flow control position of a series of at least two predetermined flow control positions of a flow control member relative to a core member. Flow control devices intended for use with an odd number of vials from a single vial and upwards employ one type of core member and flow control devices intended for use with an even number of vials from two vials and upwards, employ another type of core member. Both types preferably include an upward radial directed aspiration lumen and a downward radial directed injection lumen opposite the upward aspiration lumen relative to a horizontal longitudinal axis. The difference being that in the former, the downward radial directed injection lumen is directly opposite the upward radial directed aspiration lumen and in the latter, the downward radial directed injection lumen angled is angled with respect to the upward radial directed injection lumen so as not to be opposite thereto.

The medical apparatus includes a housing having a syringe support for horizontally supporting a syringe and a flow control device support for horizontally supporting a flow control device. The medical apparatus can be designed for either manual operation or automatic operation. In the latter case, the medical apparatus further includes a motorized syringe drive unit, a motorized flow control device drive unit and either a pre-programmed or programmable controller for controlling the motorized drive units. Pre-programmed controllers are intended to reconstitute a liquid drug according to a pre-set liquid drug reconstitution program in terms of an empty or pre-filled syringe, the number and volumetric contents of vials, injection rates and aspiration rates respectively into and from vials, and the like and/or administer a liquid drug dosage according to a pre-set liquid drug administration regime determining administration rate and administration time. Pre-programmed controllers can contain instructions for one more liquid drug reconstitution programs and one or more liquid drug administration regimes. Programmable controllers enable manual input of a liquid drug reconstitution program and/or a liquid drug administration regime.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
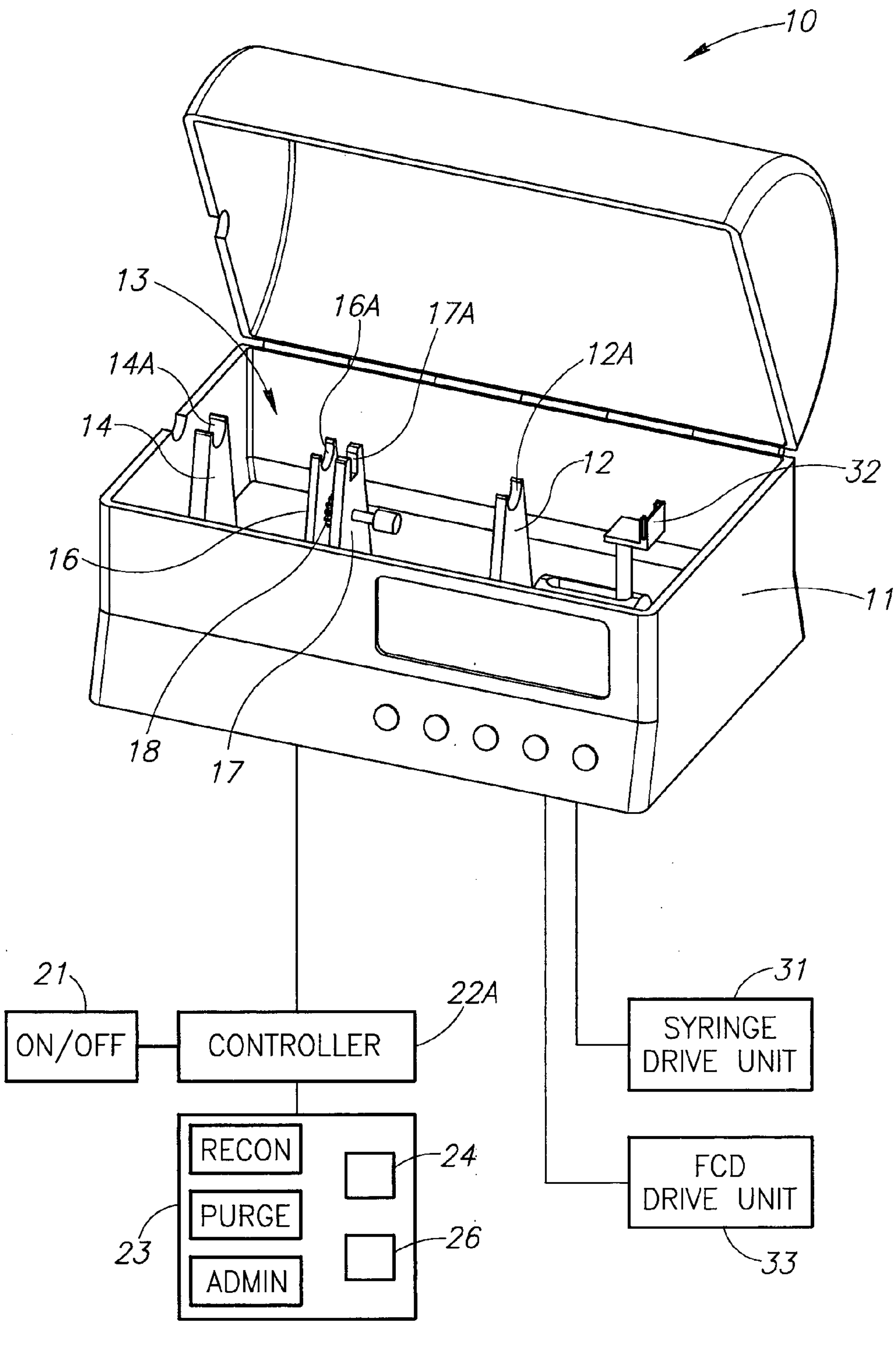
FIG. 1 shows a combined front perspective view and block diagram of medical apparatus with a pre-programmed controller for reconstituting and administrating liquid drug dosages.
Figure 2:
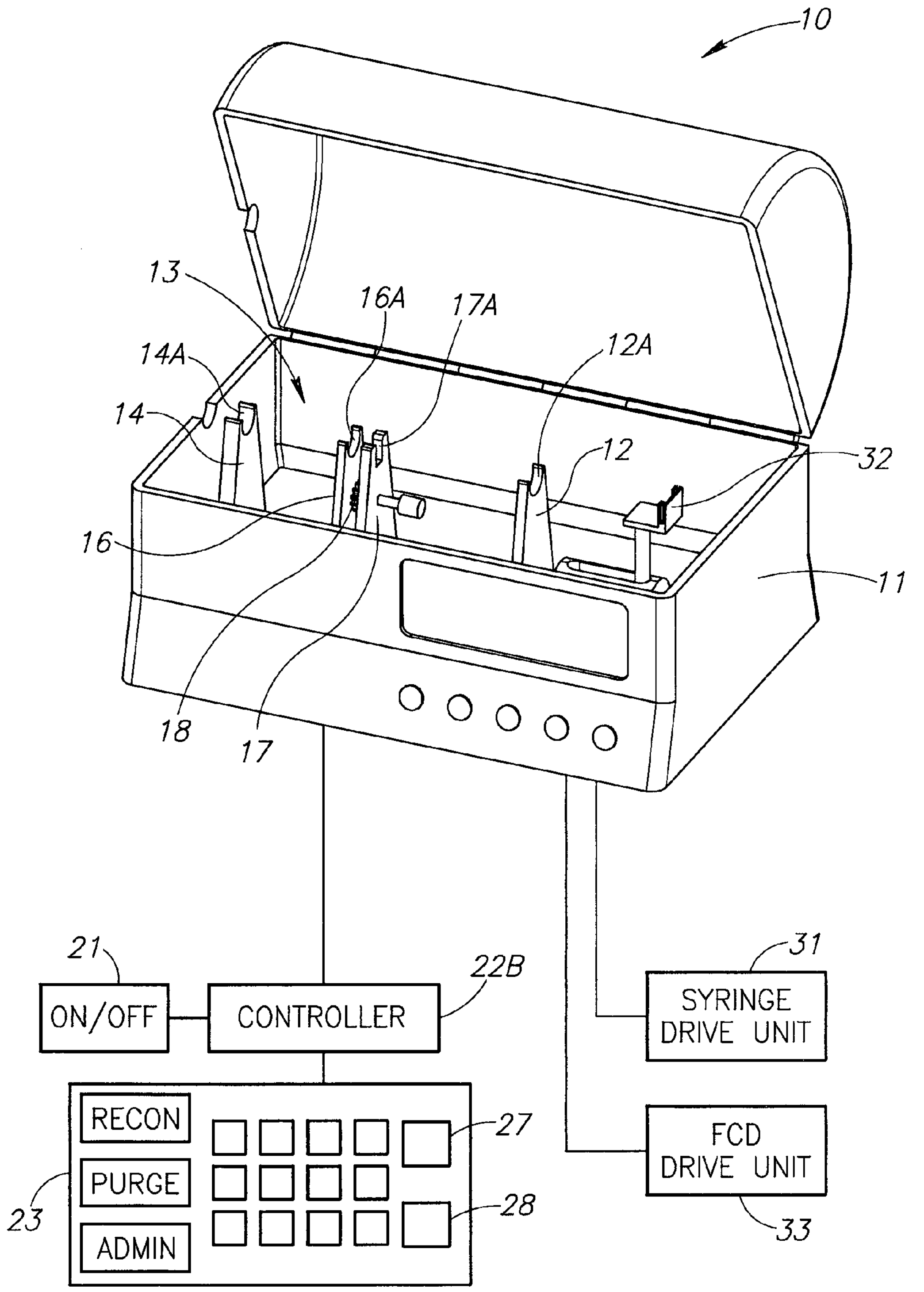
FIG. 2 shows a combined front perspective view and block diagram of medical apparatus with a programmable controller for reconstituting and administrating liquid drug dosages.

FIGS. 1 and 2 show battery or main operated medical apparatus 10 for use with kits containing a Flow Control Device (FCD), a syringe, vial adapters, and vials, for reconstituting and administrating liquid drug dosages. The medical apparatus 10 includes a housing 11 having a syringe support 12 for horizontally supporting a syringe and a flow control device support 13 for horizontally supporting a flow control device. The syringe support 12 includes an open topped slot 12A for supporting a syringe barrel's trailing end. The flow control device support 13 includes a leading stand 14 having an open topped slot 14A for supporting a flow control device's distal end and trailing stands 16 and 17 having open topped slot 16A and 17A for supporting a flow control device's proximal end. The stands 16 and 17 rotatably support a driving cogwheel 18 therebetween.

The medical apparatus 10 has an ON/OFF switch 21 and is under the control of a controller 22A or 22B. The controller 22 has a control panel 23 with three pushbuttons; "RECON" for initiating a reconstitution program, "PURGE" for purging air from an administration line, and "ADMIIN" for initiating an administration regime. FIG. 1 shows medical apparatus 10 with a pre-programmed controller 22A having one or more pre-set liquid drug reconstitution programs 24 and one or more pre-set liquid drug administration regimes 26. FIG. 2 shows medical apparatus 10 with a programmable controller

22B for enable manual input of a liquid drug reconstitution program 27 and/or a liquid drug administration regime 28. Alternatively, the control panel 23 can be a touch-screen with the above functionality.

The housing 11 includes a syringe drive unit 31 under the control of the controller 22 for reciprocating a plunger head drive member 32 forward for injection of liquid contents into a vial and administration purposes and backward for aspiration of liquid contents from a vial. The medical apparatus 10 includes a syringe linear encoder for determining the position of the plunger head drive member 32 for enabling the medical apparatus 10 to be used with syringes containing different volumes of diluent and therefore having plungers at different initial positions relative to their barrels. The controller 22 executes a syringe linear encoder reset procedure to reset the syringe linear encoder for determining the location of a syringe's plunger relative to its barrel for compensating for assembly tolerances, component tolerances, and the like. The syringe linear encoder is set to zero when a syringe's plunger tip abuts against the inside surface of its end wall.

The housing 11 includes a FCD drive unit 33 under the control of the controller 22 for rotating the driving cogwheel 18 for setting a flow control device into a predetermined series of flow control positions for reconstitution and administration purposes.

The medical apparatus 10 preferably includes a cover safety mechanism for preventing operation in the case the cover is not fully closed.

Figure 3:
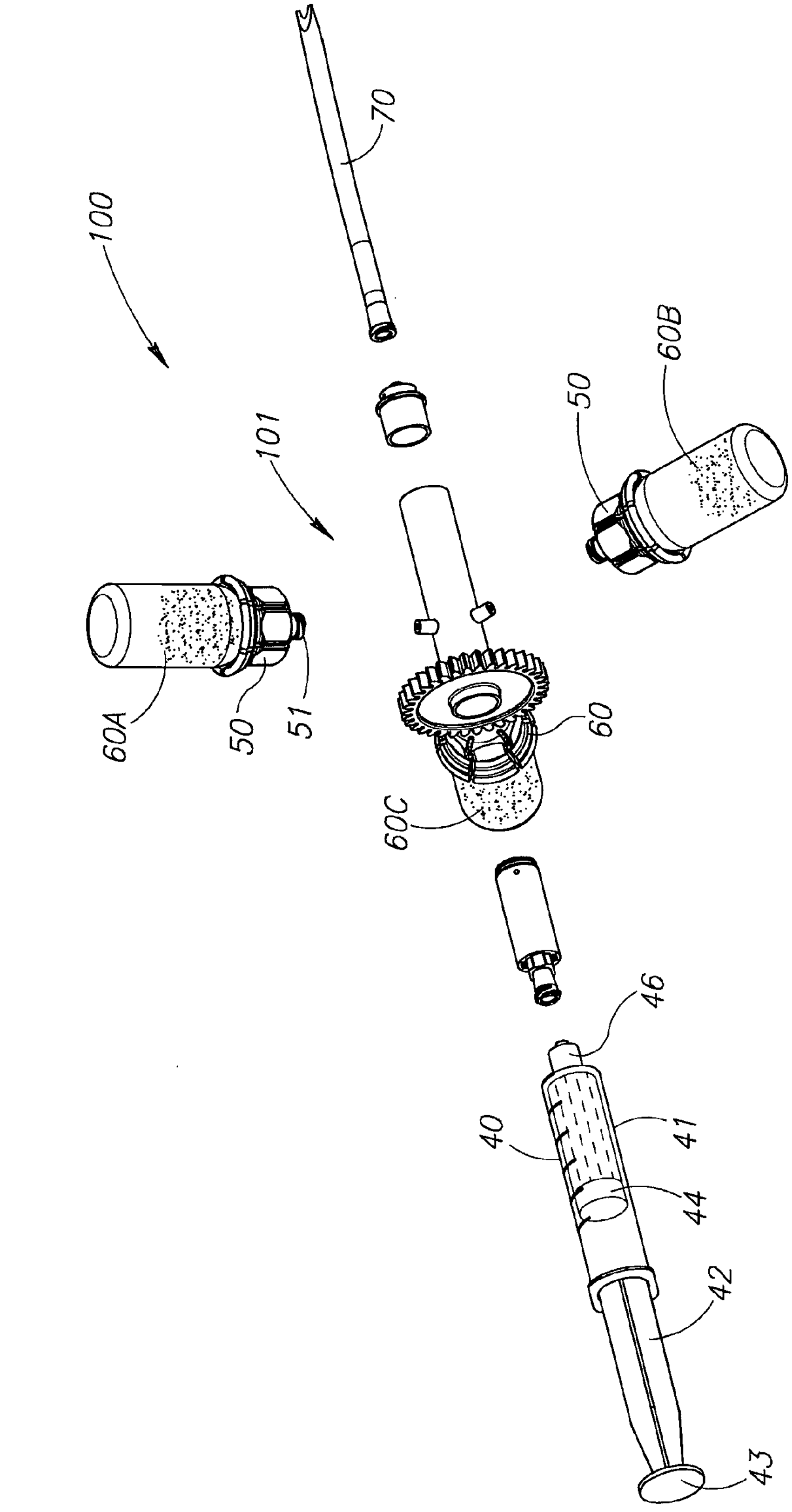
FIG. 3 shows a pictorial representation of a single use three vial kit including an exploded view of a 3 vial port flow control device having a core member, a flow control member and an end plug, a syringe, three vial adapters, three vials and an administration line.
Figure 4:
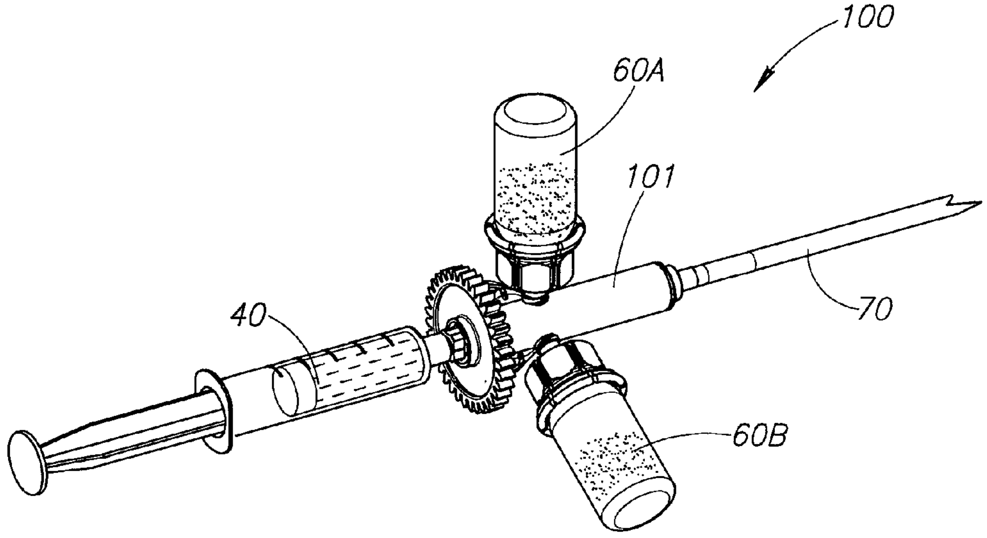
FIG. 4 shows a pictorial representation showing an assemblage of FIG. 3's kit ready for mounting in either one of FIGS. 1 and 2's medical apparatus.
Figure 5:
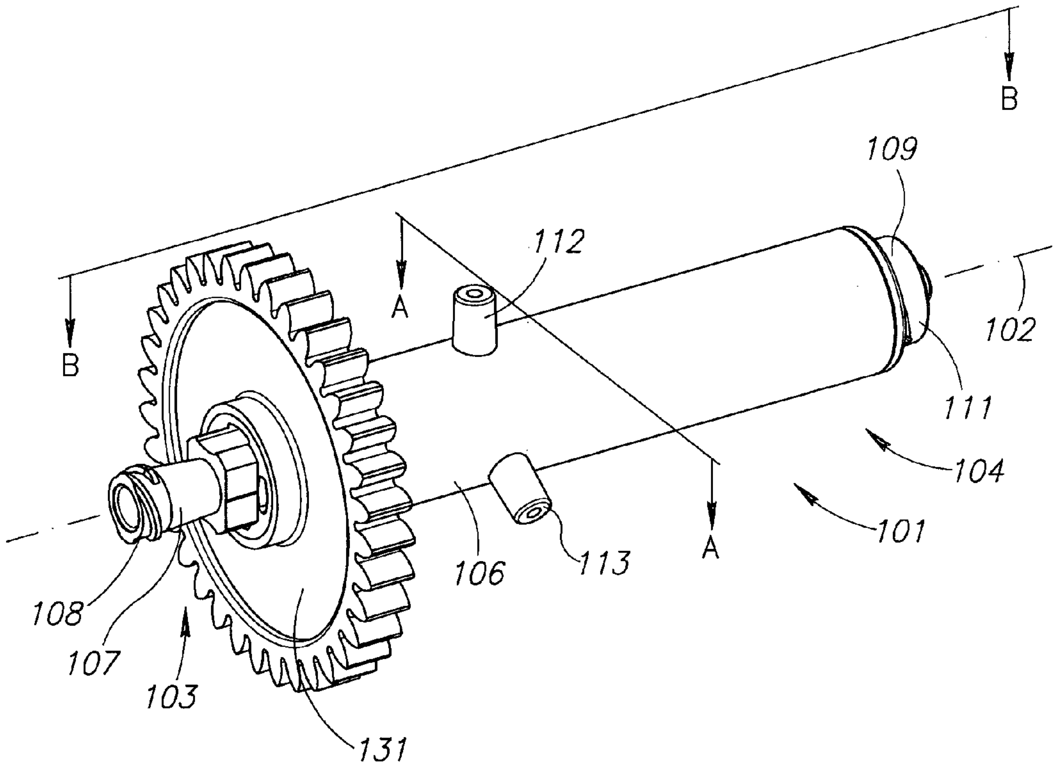
FIG. 5 shows a close up view of FIG. 3's flow control device.
Figure 6:
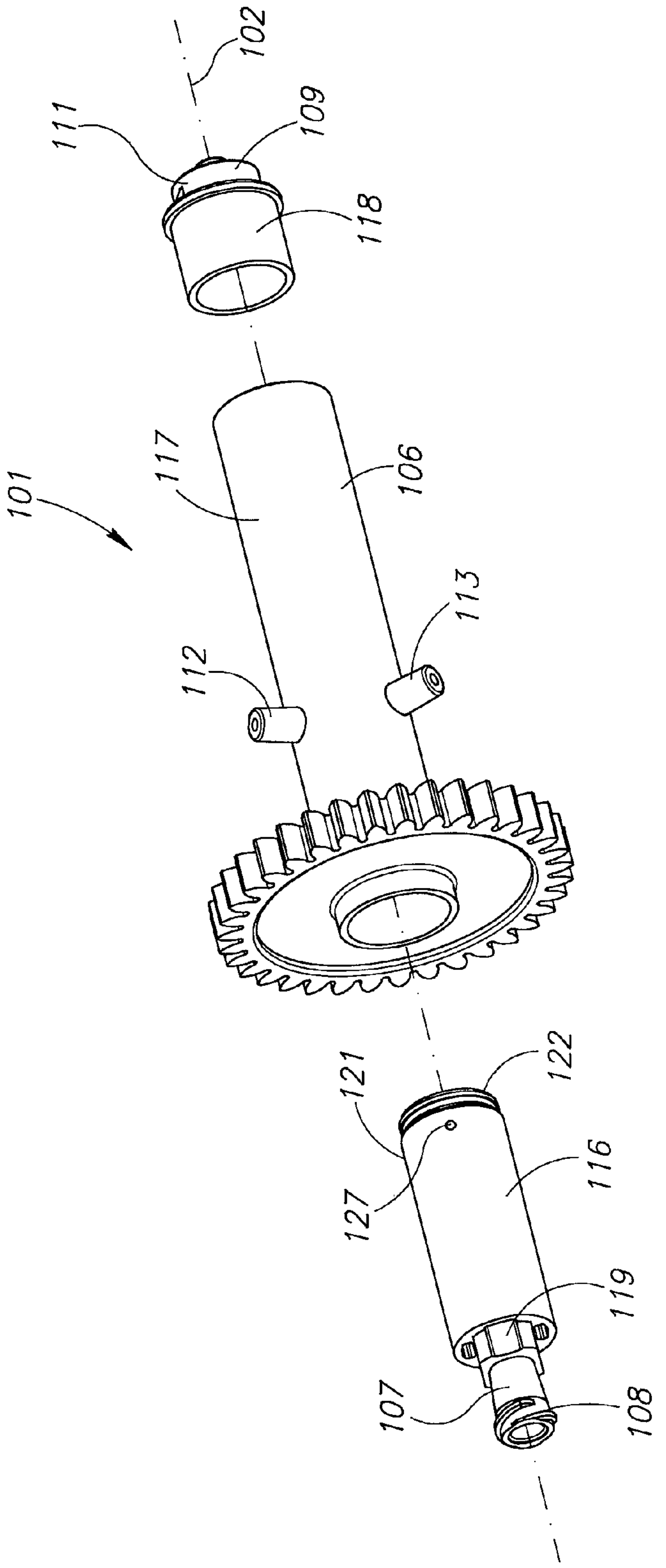
FIG. 6 is an exploded front perspective view of FIG. 3's flow control device.
Figure 7:
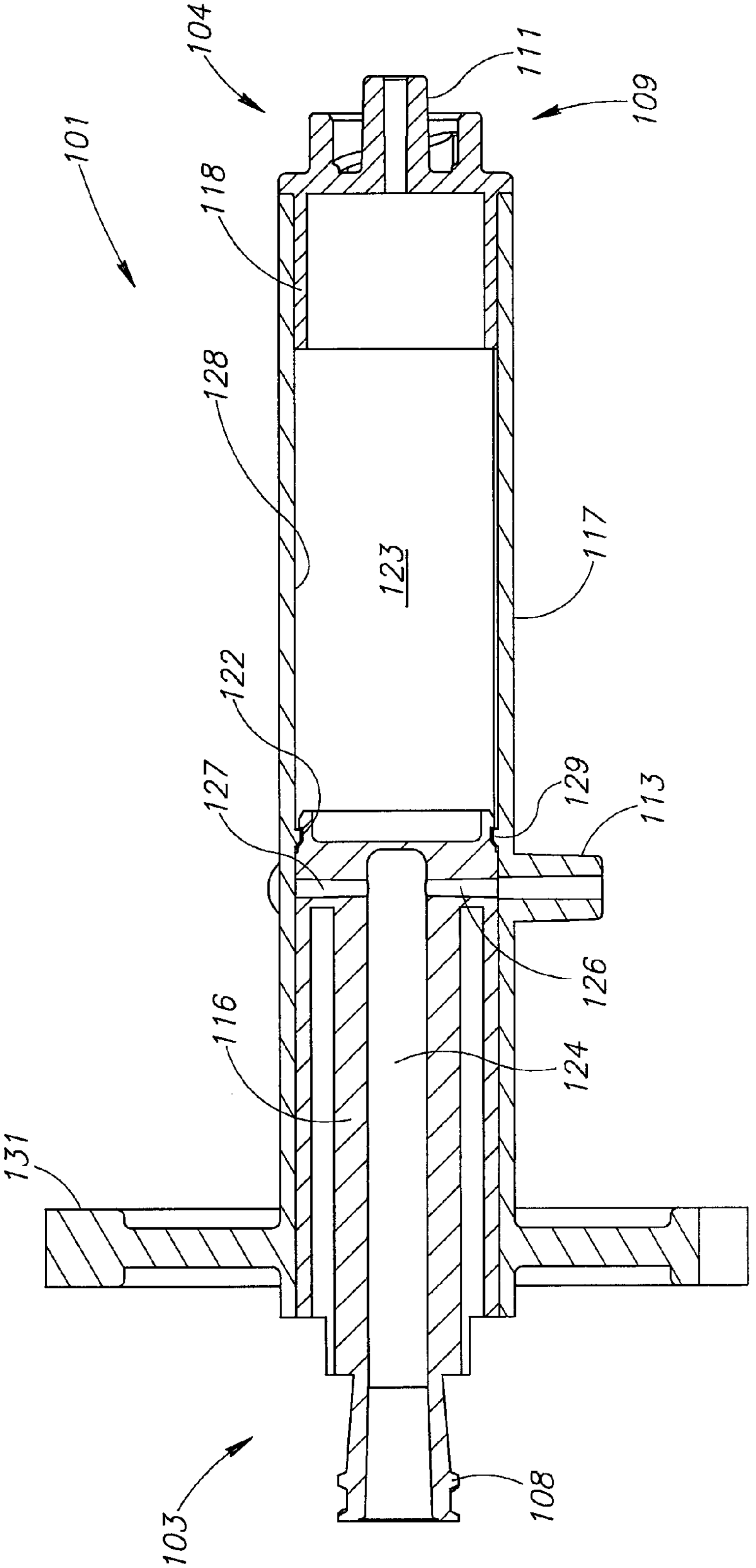
FIG. 7 shows a longitudinal cross section of FIG. 3's flow control device along line B-B in FIG. 5 for injection of liquid contents to a vial connected to a vial port.
Figure 8:
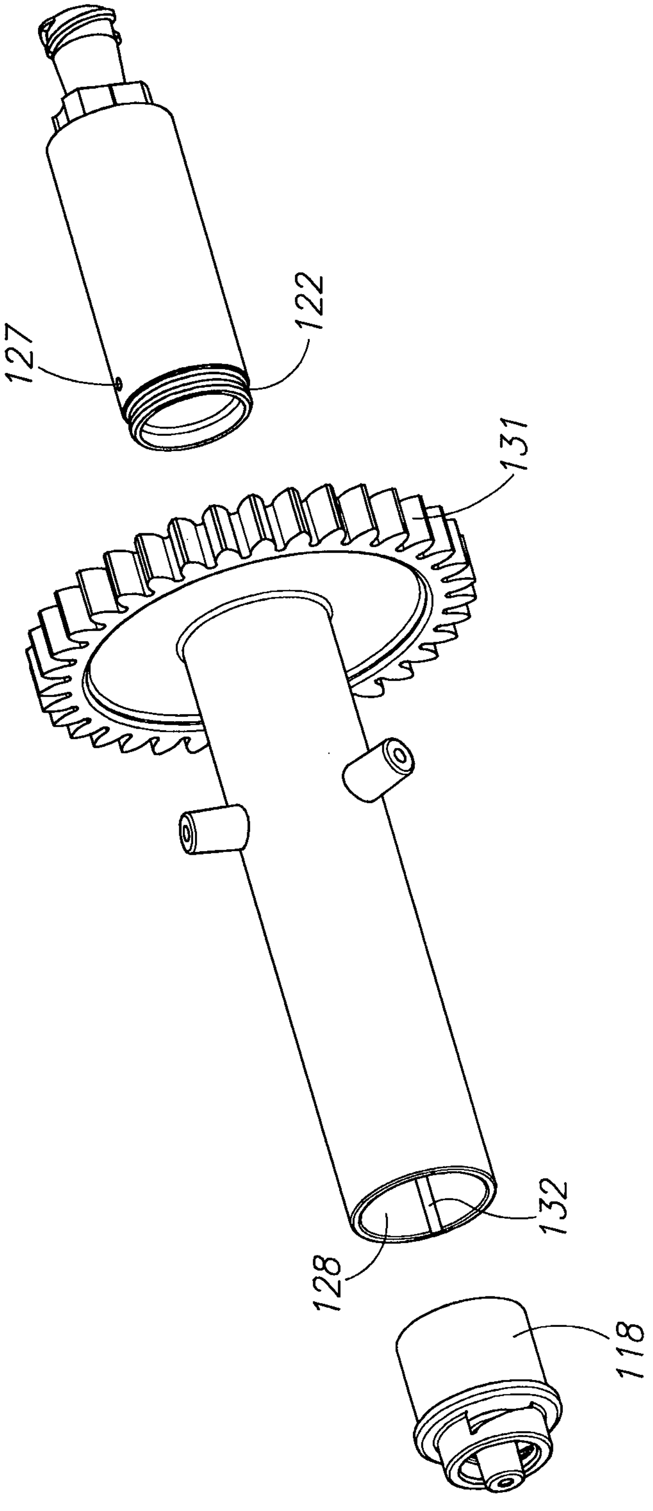
FIG. 8 is an exploded rear perspective view of FIG. 3's flow control device.

FIGS. 3 and 4 show a three vial kit 100 includes a flow control device (FCD) 101, a syringe 40 containing diluent, three vial adapters 50, three vials 60A, 60B and 60C, and an administration line 70, for example, an IV set. The syringe 40 includes a syringe barrel 41, a plunger 42 with a plunger head 43 and an elastomer plunger tip 44 for sealing the syringe barrel 41, and a male connector 46. The male connector 46 is preferably in the form of a male Luer lock connector. The three vial adapters 50 are conventional vial adapters including connectors 51, for example, commercially available from the Medimop Medical Projects Ltd, Ra'anana, Israel. The connectors 51 can be female Luer connectors as shown, male Luer connectors, and the like. Alternatively, the flow control member 101 can be integrally formed with vial adapters 50 for snap fit receiving vials, thereby simplifying assembly of the kit 100 by precluding the need to attach vial adapters to a flow control device.

The three vial kit 100 includes a syringe 40 pre-filled with diluent and three medicament containing vials 60A-60C. Alternatively, the three vial kit 100 could include an empty syringe, one diluent containing vial and two medicament containing vials. In the former case, each vial undergoes injection and subsequent aspiration of liquid contents and therefore the order of attachment of vials to vial ports is of no consequence. Against this, in the latter case, the diluent containing vial necessarily undergoes aspiration at the start of the serial reconstitution of the remaining vials.

FIGS. 5 to 8 show the flow control device 101 has a horizontal longitudinal axis 102, a proximate end 103, a distal end 104 and a cylindrical peripheral surface 106. The proximate end 103 includes an inlet port 107 with a female connector 108 for sealing engagement with the syringe's male connector 46. The female connector 108 is preferably in the form of a female Luer connector for screw thread engagement with a syringe's male Luer connector 46. The distal end 104 includes an outlet port 109 with a connector 111 for fluid connection, for example, with an IV set, and the like. The connector 111 can be a male Luer lock connector as shown, a female connector, and the like. The peripheral surface 106 has a set of three peripheral located equispaced vial ports 112, 113 and 114 midway between the inlet port 107 and the outlet port 109. The set of vial ports 112, 113 and 114 deployed at the same length therealong.

The flow control device 101 includes a stationary core member 116 co-directional with the longitudinal axis 102 and a generally tubular flow control member 117 rotatably mounted on the core member 116 and fitted with an end plug 118 including the connector 111. The core member 116 includes the inlet port 107 having a head 119 for sliding insertion into the slot 17A for mounting the core member 116 at a stationary predetermined orientation relative to the housing 11. The core member 116 has a distal end 121 extending slightly beyond the three vial ports 112, 113 and 114. The distal end 121 is formed with an annular groove 122 for snap fit mounting the flow control member 117 on the core member 116. The core member 116 bounds a cavity 123 sealed by the end plug 118. The core member 116 includes a longitudinal blind lumen 124 in flow communication with the inlet port 107. The blind lumen 124 includes a downward radial directed injection lumen 126 for facilitating injection of liquid contents into a vial in flow communication therewith. The blind lumen 124 includes an opposite upward radial directed aspiration lumen 127 for facilitating complete aspiration of the liquid contents of a vial in flow communication therewith.

The flow control member 117 has the cylindrical peripheral surface 106 and a cylindrical internal surface 128 formed with an annular flange 129 midway therealong for snap fit insertion into the annular groove 122. The peripheral surface 106 is formed with a driven cogwheel 131 towards the proximate end 103 for engaging the driving cogwheel 18 thereby enabling rotation of the flow control member 117 relative to the core member 116. The vial ports 112, 113 and 114 are disposed along the peripheral surface 106 for alignment with the injection lumen 126 and the aspiration lumen 127 at particular flow control positions of the flow control member 117 relative to the core member 116. The internal surface 128 is formed with a longitudinal directed administration flow channel 132 between the vial ports 112 and 114 for alignment with the aspiration lumen 127 at a particular flow control position of the flow control member 117 relative to the core member 116. The administration flow channel 132 extends midway along the internal surface 128 to the distal end 104.

Figure 9A:
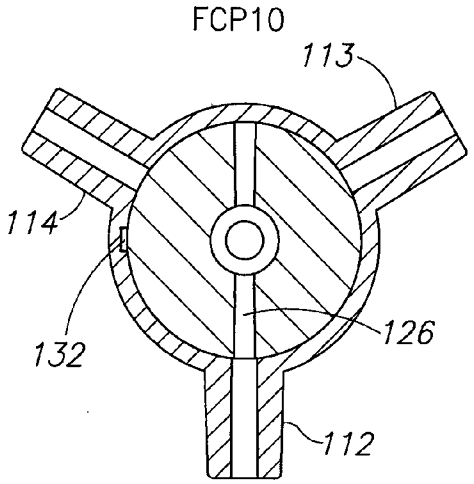
FIG. 9A shows a transverse cross section of FIG. 3's flow control device along line A-A in FIG. 5 in a first flow control position for injection of liquid contents to a vial connected to its first vial port.
Figure 10A:
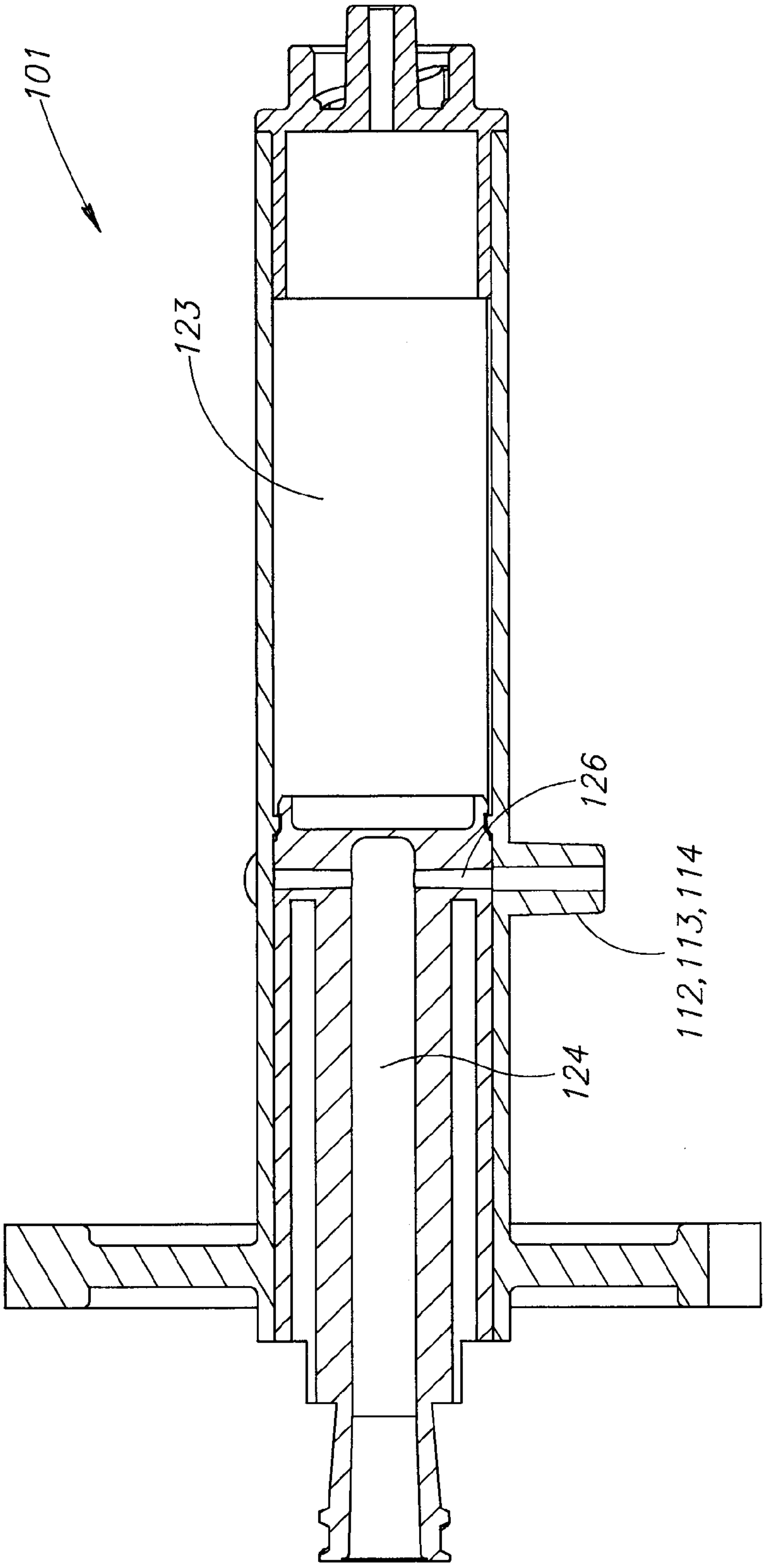
FIG. 10A shows a longitudinal cross section of FIG. 3's flow control device along line B-B in FIG. 5 for injection of liquid contents to a vial connected to a vial port.

The flow control device 101 has seven Flow Control Positions (FCPs) as now described with reference to FIGS. 9A to 9G and FIGS. 10A to 10C as follows:

FCP 10 denoting alignment of the vial port 112 with the injection lumen 126 for injection of liquid contents to a vial 60 connected to the vial port 112 as shown in FIGS. 9A and 10A.

Figure 9B:
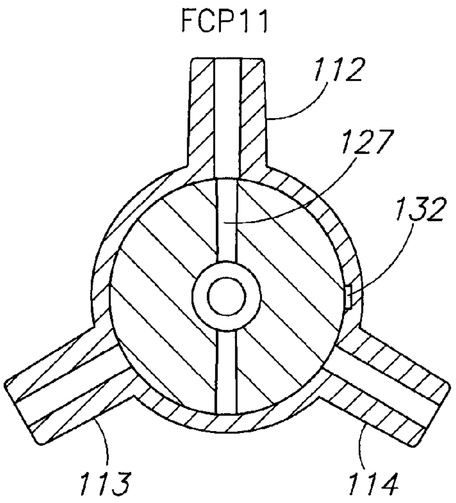
FIG. 9B shows a transverse cross section of FIG. 3's flow control device along line A-A in FIG. 5 in a second flow control position for aspiration of liquid contents from a vial connected to its first vial port.
Figure 10B:
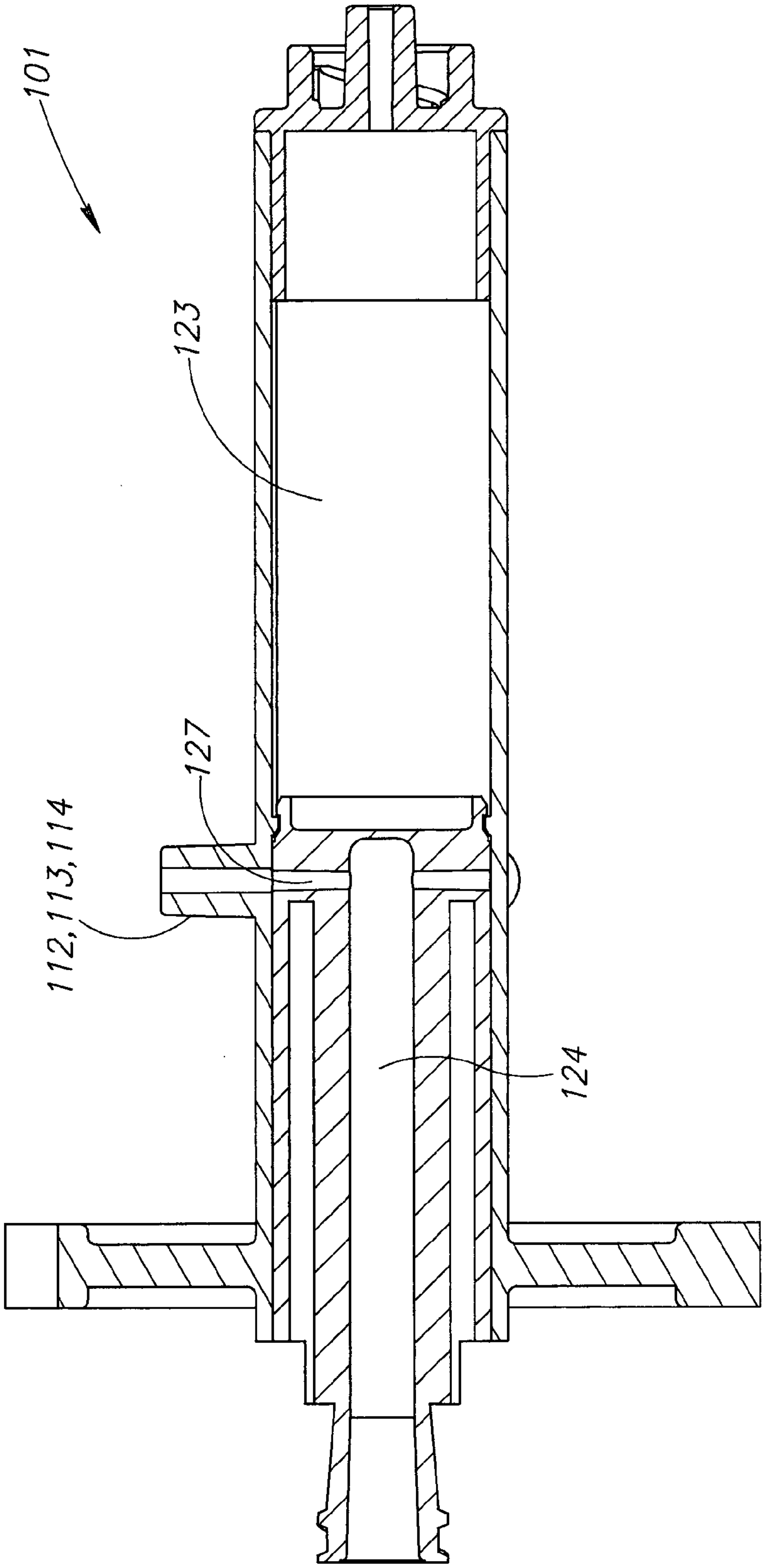
FIG. 10B shows a longitudinal cross section of FIG. 3's flow control device along line B-B in FIG. 5 for aspiration of liquid contents from a vial connected to a vial port.

FCP 11 denoting alignment of the vial port 112 with the aspiration lumen 127 for aspiration of liquid contents from a vial 60 connected to the vial port 112 as shown in FIGS. 9B and 10B.

Figure 9C:
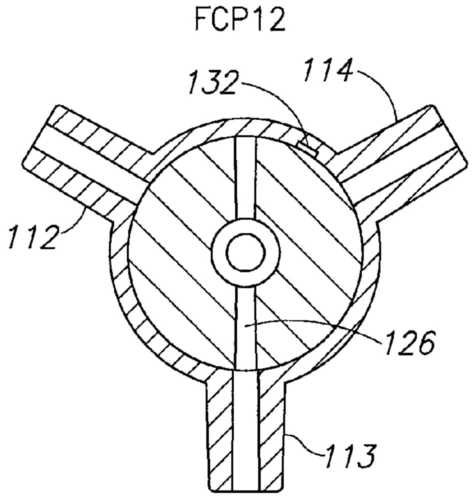
FIG. 9C shows a transverse cross section of FIG. 3's flow control device along line A-A in FIG. 5 in a third flow control position for injection of liquid contents to a vial connected to its second vial port.

FCP 12 denoting alignment of the vial port 113 with the injection lumen 126 for injection of liquid contents to a vial 60 connected to the vial port 113 as shown in FIGS. 9C and 10A.

Figure 9D:
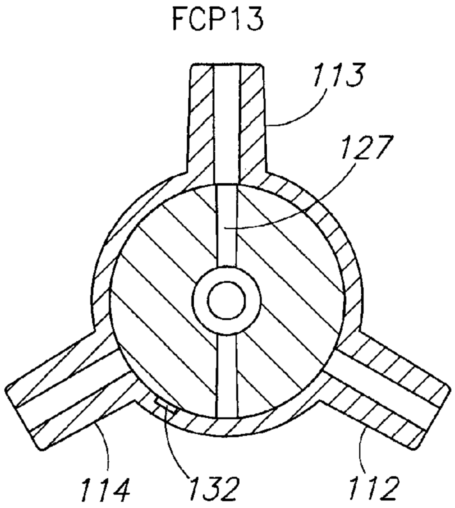
FIG. 9D shows a transverse cross section of FIG. 3's flow control device along line A-A in FIG. 5 in a fourth flow control position for aspiration of liquid contents from a vial connected to its second vial port.

FCP 13 denoting alignment of vial port 113 with the aspiration lumen 127 for aspiration of liquid contents from a vial 60 connected to the vial port 113 as shown in FIGS. 9D and 10B.

Figure 9E:
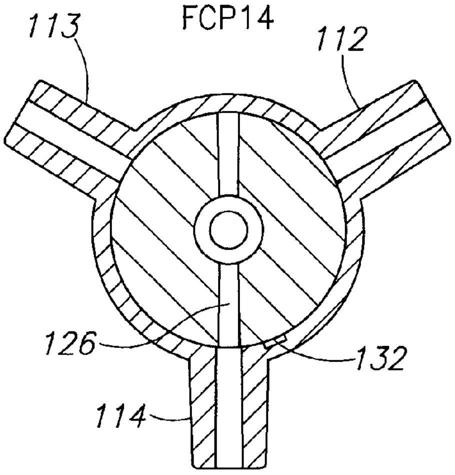
FIG. 9E shows a transverse cross section of FIG. 3's flow control device along line A-A in FIG. 5 in a fifth flow control position for injection of liquid contents to a vial connected to its third vial port.

FCP 14 denoting alignment of vial port 114 with the injection lumen 126 for injection of liquid contents to a vial 60 connected to the vial port 114 as shown in FIGS. 9E and 10A.

Figure 9F:
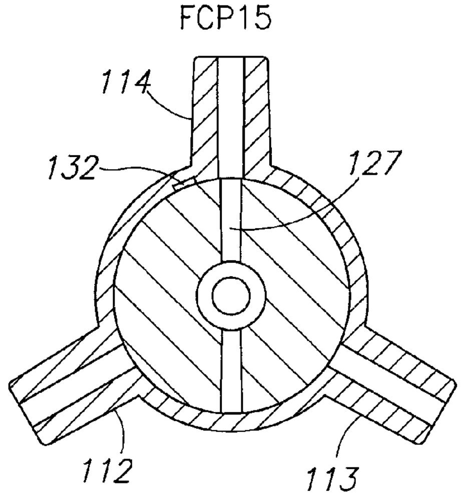
FIG. 9F shows a transverse cross section of FIG. 3's flow control device along line A-A in FIG. 5 in a sixth flow control position for aspiration of liquid contents from a vial connected to its third vial port.

FCP 15 denoting alignment of the vial port 114 with the aspiration lumen 127 for aspiration of liquid contents from a vial 60 connected to the vial port 114 as shown in FIGS. 9F and 10B.

Figure 9G:
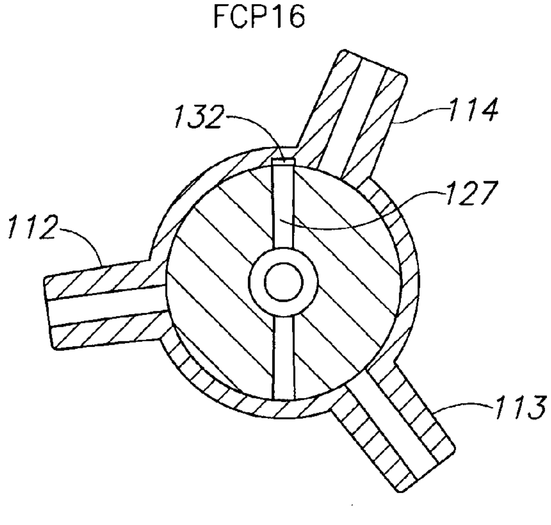
FIG. 9G shows a transverse cross section of FIG. 3's flow control device along line A-A in FIG. 5 in a seventh flow control position for dosage administration.
Figure 10C:
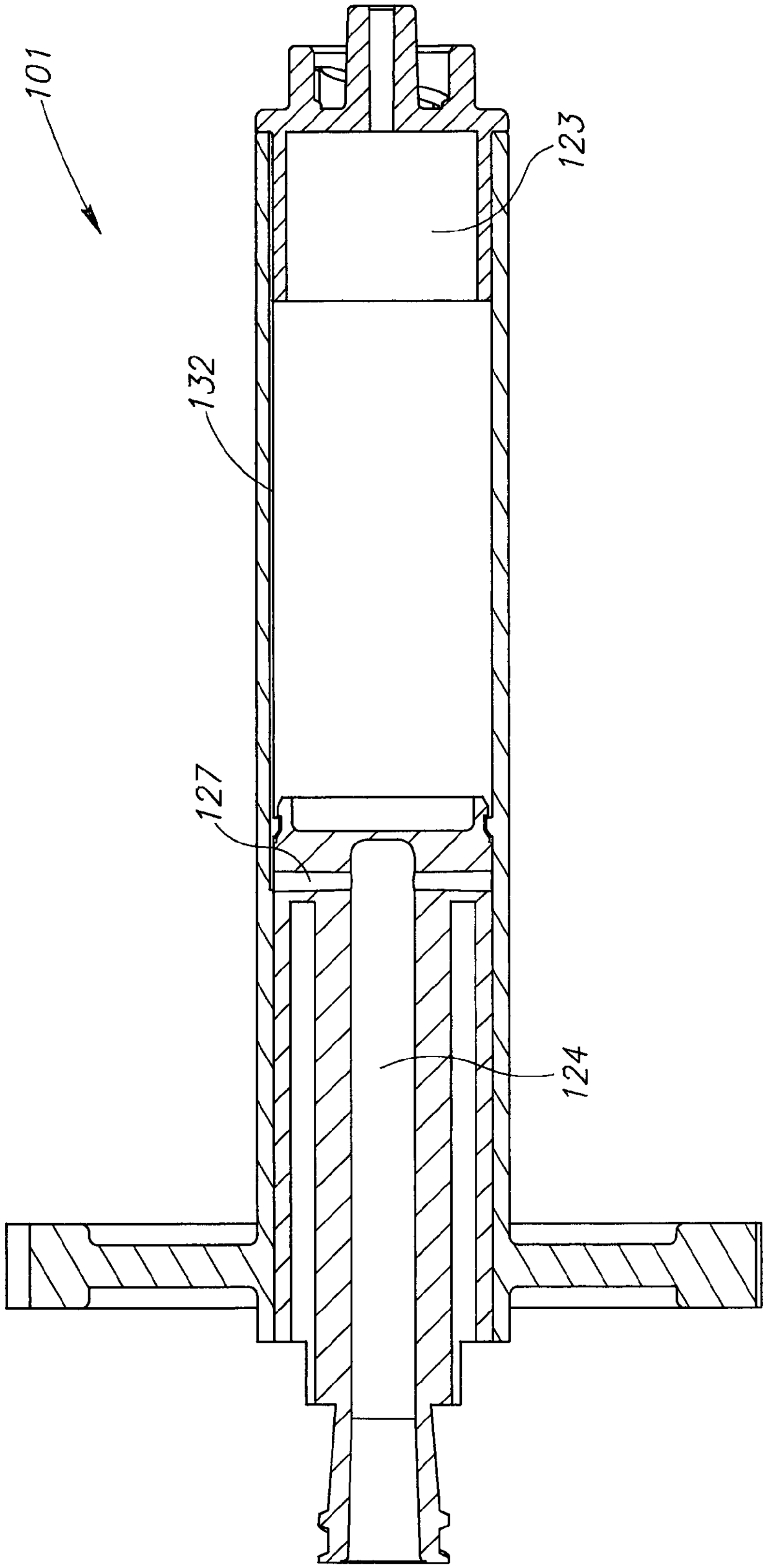
FIG. 10C shows a longitudinal cross section of FIG. 3's flow control device along line B-B in FIG. 5 for dosage administration.

FCP 16 denoting alignment of the administration flow channel 132 with the aspiration lumen 127 for injection of liquid contents to the outlet port 109 for dosage administration as shown in FIGS. 9G and 10C.

Figure 11:
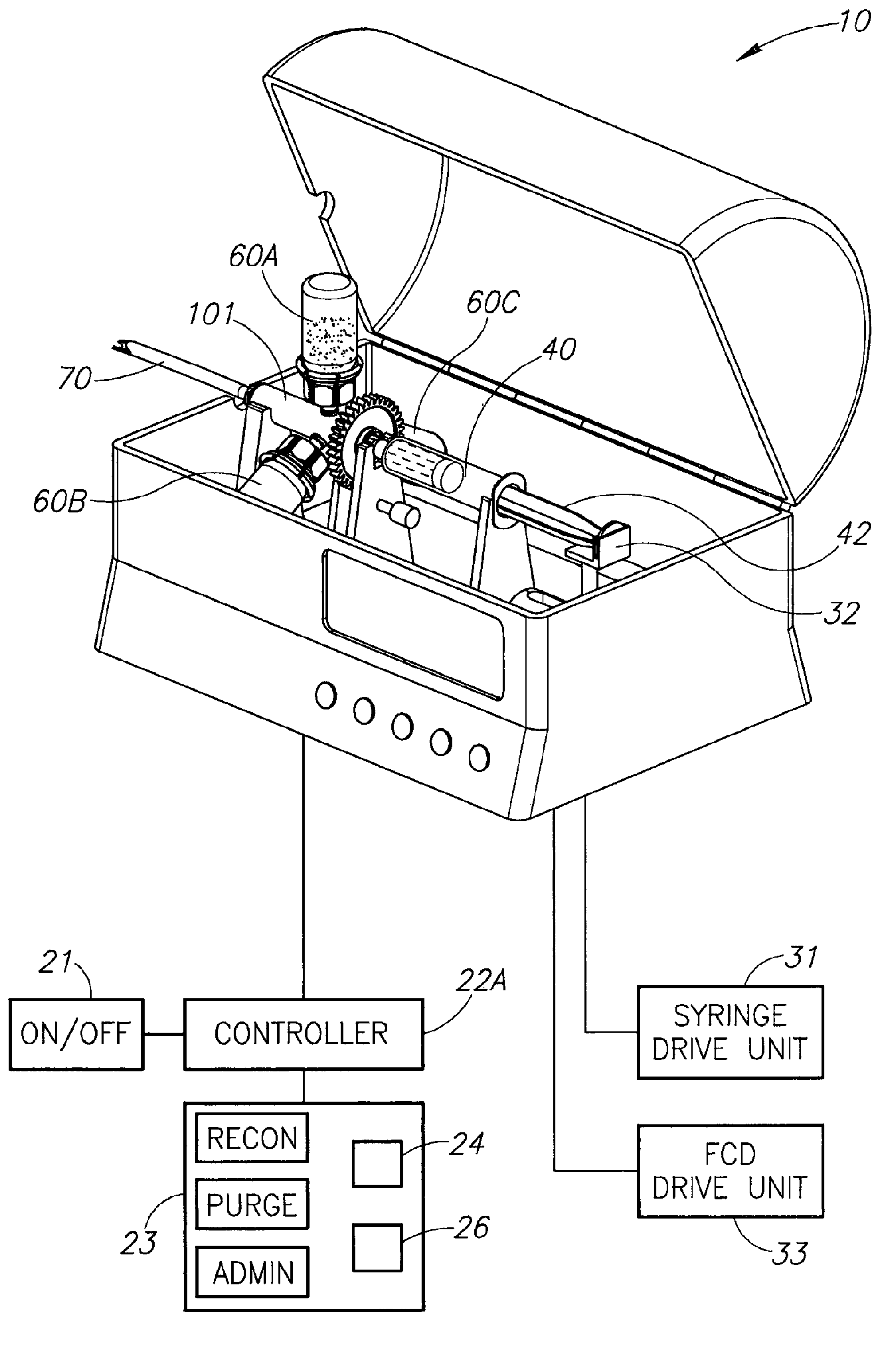
FIG. 11 shows a front perspective view of FIG. 1's medical apparatus having an assembled three vial kit with its syringe's plunger in its most backward position.
Figure 12:
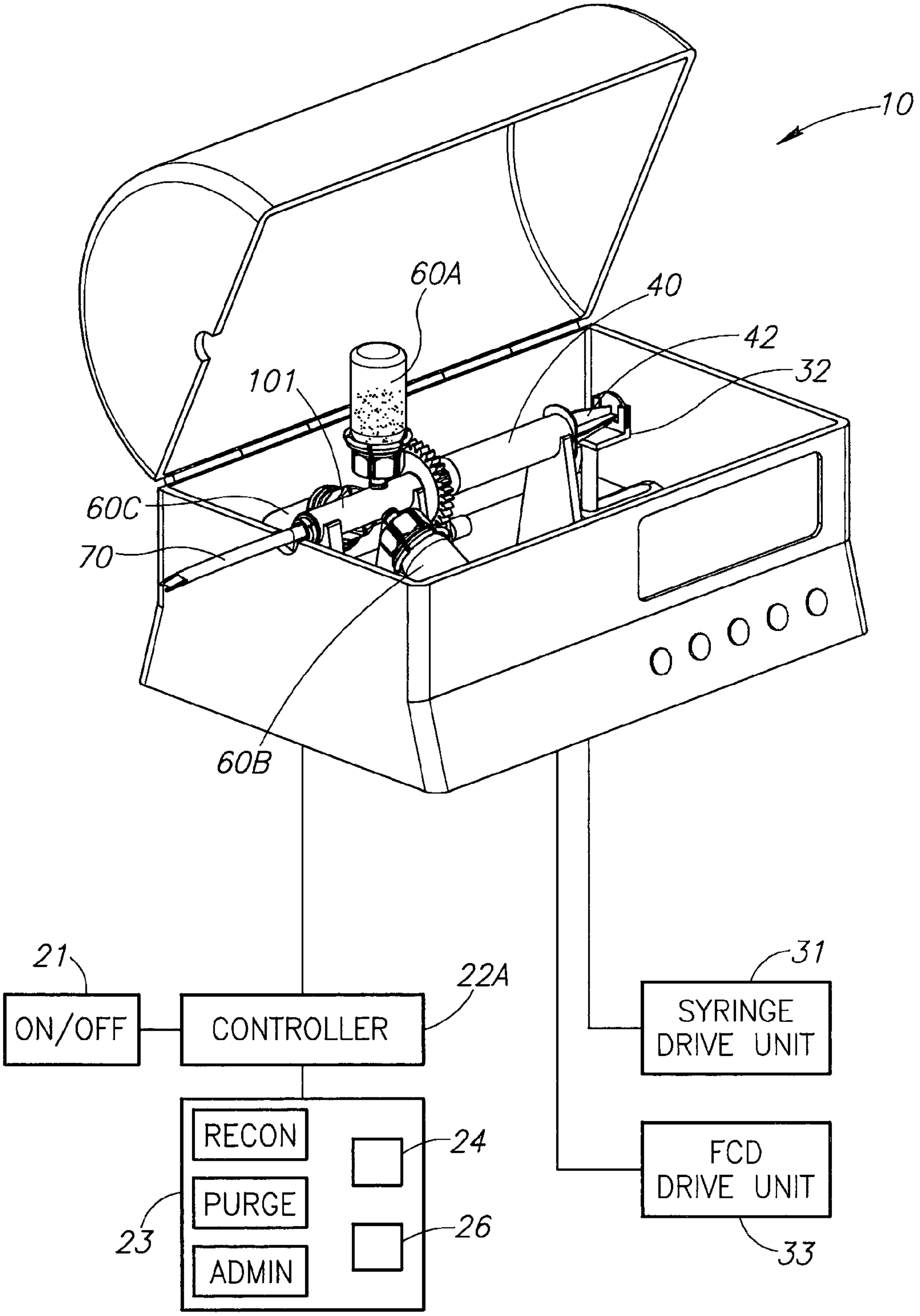
FIG. 12 shows a rear perspective view of FIG. 1's medical apparatus having an assembled three vial kit with its syringe's plunger in its most forward position.

FIGS. 11 and 12 show the two operative positions of the plunger head drive member 32 for fully withdrawing the plunger 42 to its most rearward position for aspirating liquid contents and fully depressing the plunger 42 to its most forward position for injecting liquid contents.

The operation of the medical apparatus 10 with the preprogrammed controller 22A and a three vial kit 100 including a pre-filled syringe 40 and three medicament containing vials 60A, 60B and 60C includes the following steps:

Step 1: The kit 100 is supplied with its flow control device 101 in its first flow control position FCP 10 for setting flow connection with the vial port 112

Step 2: User attaches the vials 60A-60C to the vial adapters 50

Step 3: User attaches the vials 60A-60C to the vial ports 112, 113 and 114, respectively Step 4: User attaches the syringe 40 onto the flow control device 101

Step 5: User sets the medical apparatus 10 such that its plunger head drive member 32 is in its most backward position and mounts the assembled three vial kit 100 on the medical apparatus 10

Step 6: User presses the "RECON" pushbutton

Step 7: Medical apparatus 10 fully depresses the plunger 42 to inject diluent into the vial 60A Step 8: Medical apparatus 10 reciprocates the flow control member 117 back and forth for agitating the vial 60A for reconstituting its powder contents Step 9: Medical apparatus 10 rotates the flow control member 117 to set the flow control device 101 to its second flow control position FCP 11 ready for aspiration from the vial 60A Step 10: Medical apparatus 10 withdraws the plunger 42 to aspirate the vial 60A's liquid drug contents to the syringe 40

Step 11: Medical apparatus 10 rotates the flow control member 117 to set the flow control device 101 to its third flow control position FCP 12 ready for injection of the liquid drug contents into the vial 60B Step 12: Medical apparatus 10 fully depresses the plunger 42 to inject liquid drug contents into the vial 60B Step 13: Medical apparatus 10 reciprocates the flow control member 117 back and forth for agitating the vial 60B for reconstituting its powder contents Step 14: Medical apparatus 10 rotates the flow control member 117 to set the flow control device 101 to its fourth flow control position FCP 13 ready for aspiration from the vial 60B Step 15: Medical apparatus 10 withdraws the plunger 42 to aspirate the vial 60B's liquid drug contents to the syringe 40

Step 16: Medical apparatus 10 rotates the flow control member 117 to set the flow control device 101 to its fifth now control position FCP 14 ready for injection of the liquid drug contents into the vial 60C Step 17: Medical apparatus 10 fully depresses the plunger 42 to inject the liquid drug contents into the vial 60C Step 18: Medical apparatus 10 reciprocates the flow control member 117 back and forth for agitating vial 60C for reconstituting its powder contents Step 19: Medical apparatus 10 rotates the flow control member 117 to set the flow control device 101 to its sixth flow control position FCP 15 ready for aspiration from the vial 60C Step 20: Medical apparatus 10 withdraws the plunger 42 to aspirate the vial 60C's liquid drug contents to the syringe 40

Step 21: Medical apparatus 10 rotates the flow control member 117 to set the flow control device 101 to its seventh flow control position FCP 16 ready for dosage administration Step 22: User attaches the administration line 70 to the outlet port 109

Step 23: User presses "PURGE" pushbutton

Step 24: Medical apparatus 10 depresses the plunger 42 to purge air from the administration line 70

Figure 13:
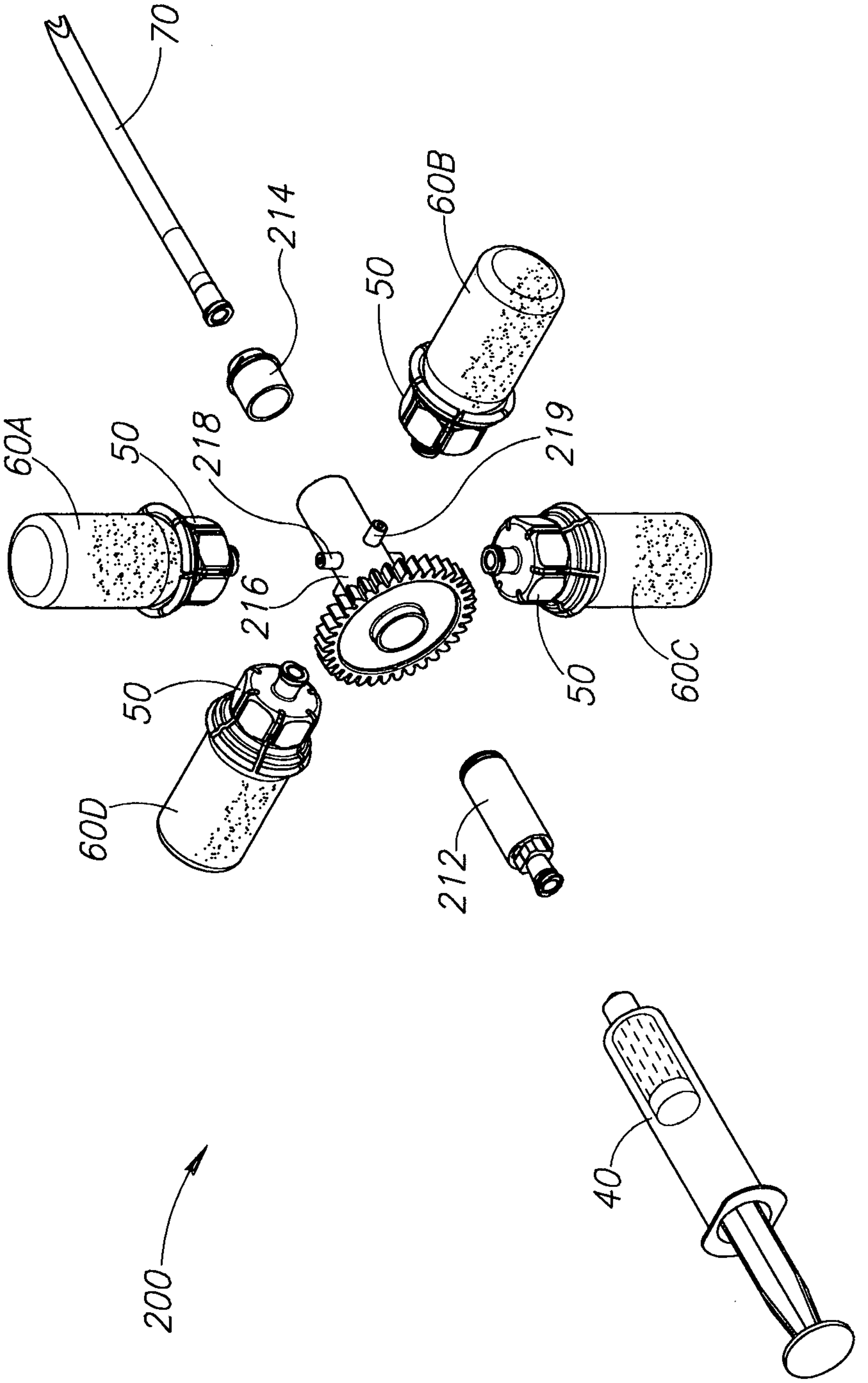
FIG. 13 shows a pictorial representation of a single use four vial kit including an exploded view of a 4 vial port flow control device having a core member, a flow control member and an end plug, a syringe, four vial adapters, four vials and an administration line.
Figure 14:
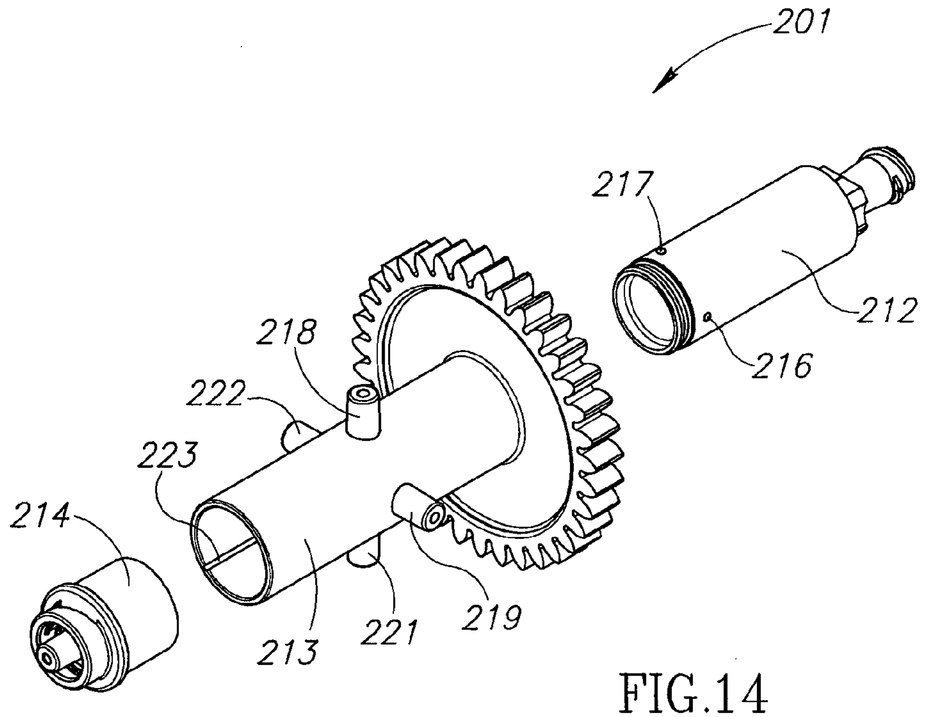
FIG. 14 is an exploded rear perspective view of FIG. 13's flow control device.
Figure 15:
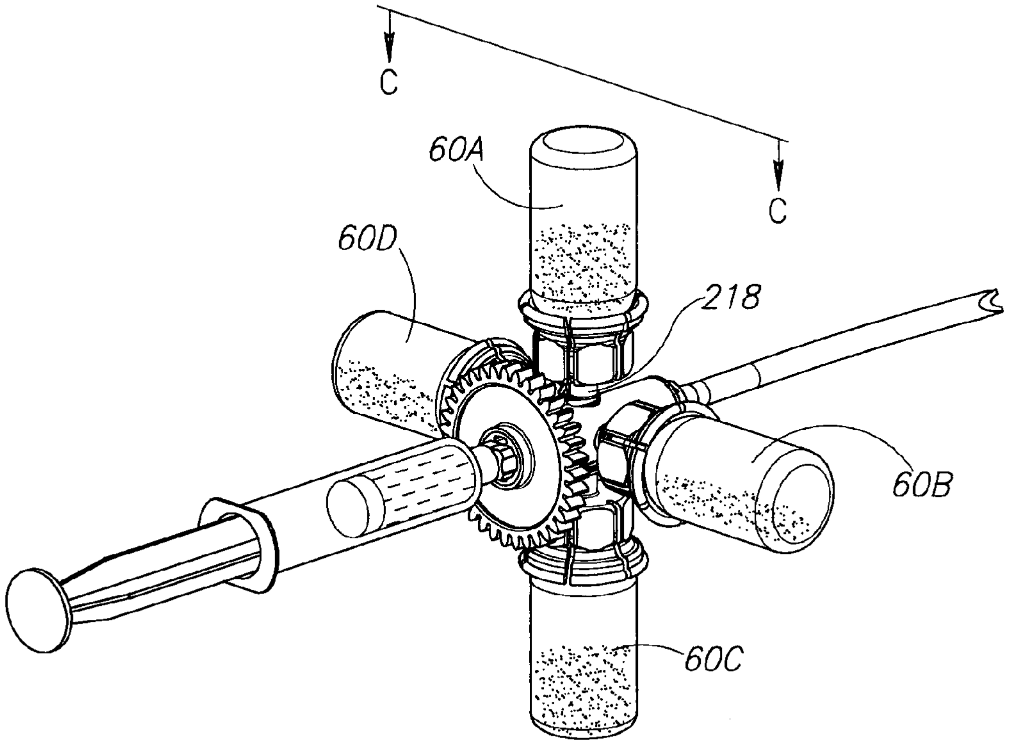
FIG. 15 shows a pictorial representation showing an assemblage of FIG. 13's kit ready for mounting in either one of FIGS. 1 and 2's medical apparatus.

Step 25: User attaches the administration line 70 to patient's vein via an administration device, for example, a needle, and the like Step 26: User presses the "ADMIN" pushbutton to start dosage administration to patient Step 27: Medical apparatus 10 fully depresses the plunger 42 for dosage administration FIGS. 13 to 15 show a four vial kit 200 including a four vial flow control device 201, a syringe 40, four vial adapters 50 and four vials 60D, 60E, 60F and 60G. The flow control device 201 has a similar construction to the flow control device 101 and includes a horizontal longitudinal axis 202, a proximate end 203, a distal end 204 and a cylindrical peripheral surface 206. The proximate end 203 includes an inlet port 207 with a connector 208 for screw thread engagement with the syringe's connector 46. The distal end 204 includes an outlet port 209 with a connector 211 for fluid connection, for example, with an IV set, and the like. The flow control device 201 includes a stationary core member 212 and a generally tubular flow control member 213 rotatably mounted on the core member 212 and fitted with an end plug 214 including the male Luer lock connector 211.

The core member 212 includes a longitudinal blind lumen 216 having a downward radial directed injection lumen 216 for facilitating injection of liquid contents into a vial in flow communication therewith and an upward radial directed aspiration lumen 217 for facilitating complete aspiration of the liquid contents of a vial in flow communication therewith. The flow control member 213 includes four equispaced vial ports 218, 219, 221 and 222 for flow communication with the injection lumen 216 and the aspiration lumen 217 at particular flow control positions of the flow control member 213 relative to the core member 212. The injection lumen 216 and the aspiration lumen 217 are not diametrically opposite to preclude the inlet port 207 being in simultaneous flow communication with two vial ports. The flow control member 213 includes an administration flow channel 223 similar to the administration flow channel 132. The administration flow channel 223 is disposed between the vial ports 218 and 222.

Figure 16A:
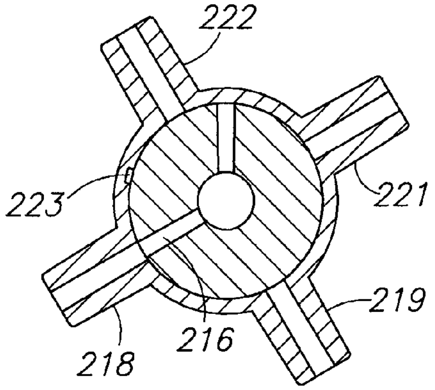
FIG. 16A shows a transverse cross section of FIG. 13's flow control device along line C-C in FIG. 15 in a first flow control position for injection of liquid contents to a vial connected to its first vial port.

The flow control device 201 has nine Flow Control Positions (FCPs) as follows:

FCP 20 denoting alignment of the vial port 218 with the injection lumen 216 for injection of liquid contents to a vial 60 connected to the vial port 218 as shown in FIG. 16A.

Figure 16B:
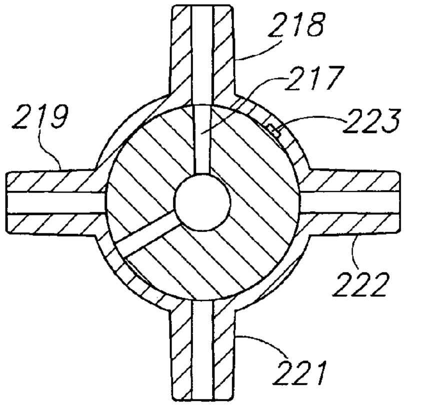
FIG. 16B shows a transverse cross section of FIG. 13's flow control device along line C-C in FIG. 15 in a second flow control position for aspiration of liquid contents from a vial connected to its first vial port.

FCP 21 denoting alignment of the vial port 218 with the aspiration lumen 217 for aspiration of liquid contents from a vial 60 connected to the vial port 218 as shown in FIG. 16B.

Figure 16C:
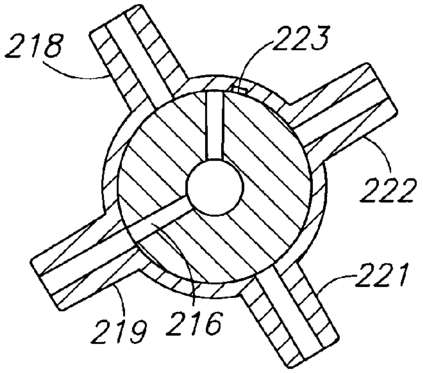
FIG. 16C shows a transverse cross section of FIG. 13's flow control device along line C-C in FIG. 15 in a third flow control position for injection of liquid contents to a vial connected to its second vial port.

FCP 22 denoting alignment of the vial port 219 with the injection lumen 216 for injection of liquid contents to a vial 60 connected to the vial port 219 as shown in FIG. 16C.

Figure 16D:
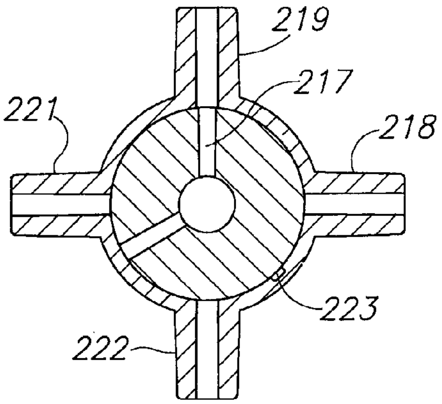
FIG. 16D shows a transverse cross section of FIG. 13's flow control device along line C-C in FIG. 15 in a fourth flow control position for aspiration of liquid contents from a vial connected to its second vial port.

FCP 23 denoting alignment of the vial port 219 with the aspiration lumen 217 for aspiration of liquid contents from a vial 60 connected to the vial port 219 as shown in FIG. 16D.

Figure 16E:
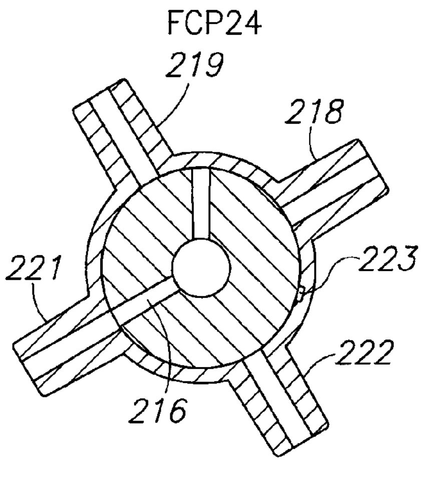
FIG. 16E shows a transverse cross section of FIG. 13's flow control device along line C-C in FIG. 15 in a fifth flow control position for injection of liquid contents to a vial connected to its third vial port.

FCP 24 denoting alignment of the vial port 221 with the injection lumen 216 for injection of liquid contents to a vial 60 connected to the vial port 221 as shown in FIG. 16E.

Figure 16F:
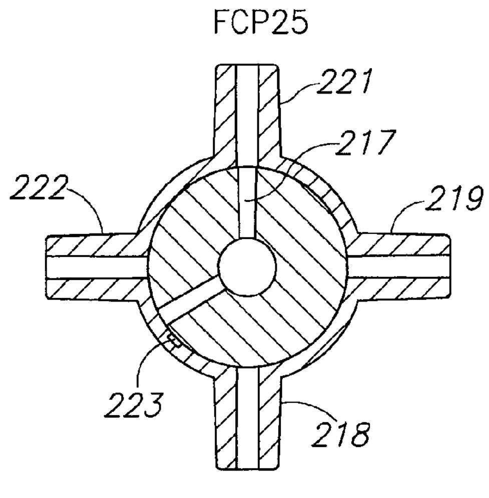
FIG. 16F shows a transverse cross section of FIG. 13's flow control device along line C-C in FIG. 15 in a sixth flow control position for aspiration of liquid contents from a vial connected to its third vial port.

FCP 25 denoting alignment of the vial port 221 with the aspiration lumen 217 for aspiration of liquid contents from a vial 60 connected to the vial port 221 as shown in FIG. 16F.

Figure 16G:
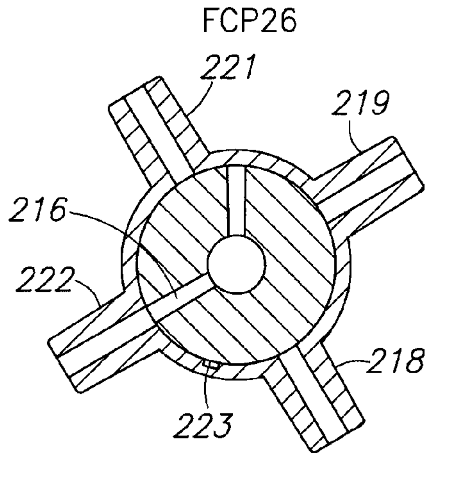
FIG. 16G shows a transverse cross section of FIG. 13's flow control device along line C-C in FIG. 15 in a seventh flow control position for injection of liquid contents to a vial connected to its fourth vial port.

FCP 26 denoting alignment of the vial port 222 with the injection lumen 216 for injection of liquid contents to a vial 60 connected to the vial port 222 as shown in FIG. 16G.

Figure 16H:
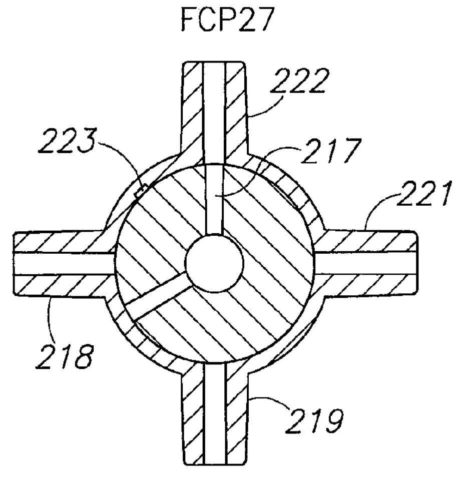
FIG. 16H shows a transverse cross section of FIG. 13's flow control device along line C-C in FIG. 15 in: an eighth flow control position for aspiration of liquid contents from a vial connected to its fourth vial port.

FCP 27 denoting alignment of the vial port 222 with the aspiration lumen 217 for aspiration of liquid contents from a vial 60 connected to the vial port 222 as shown in FIG. 16H.

Figure 16I:
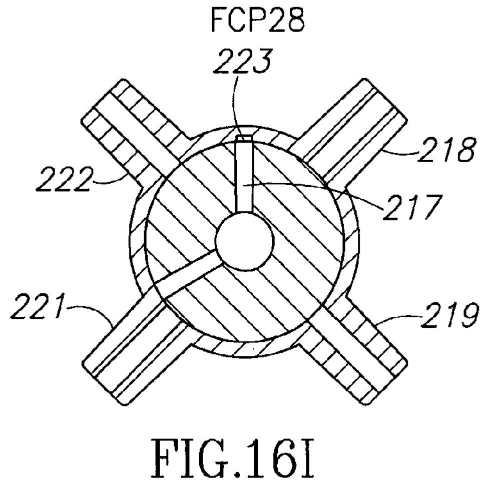
FIG. 16I shows a transverse cross section of FIG. 13's flow control device along line C-C in FIG. 15 in a ninth flow control position for dosage administration.

FCP 28 denoting alignment of the administration flow channel 223 with the aspiration lumen 217 for injection of liquid contents to the outlet port 209 for dosage administration as shown in FIG. 16I.

Figure 17:
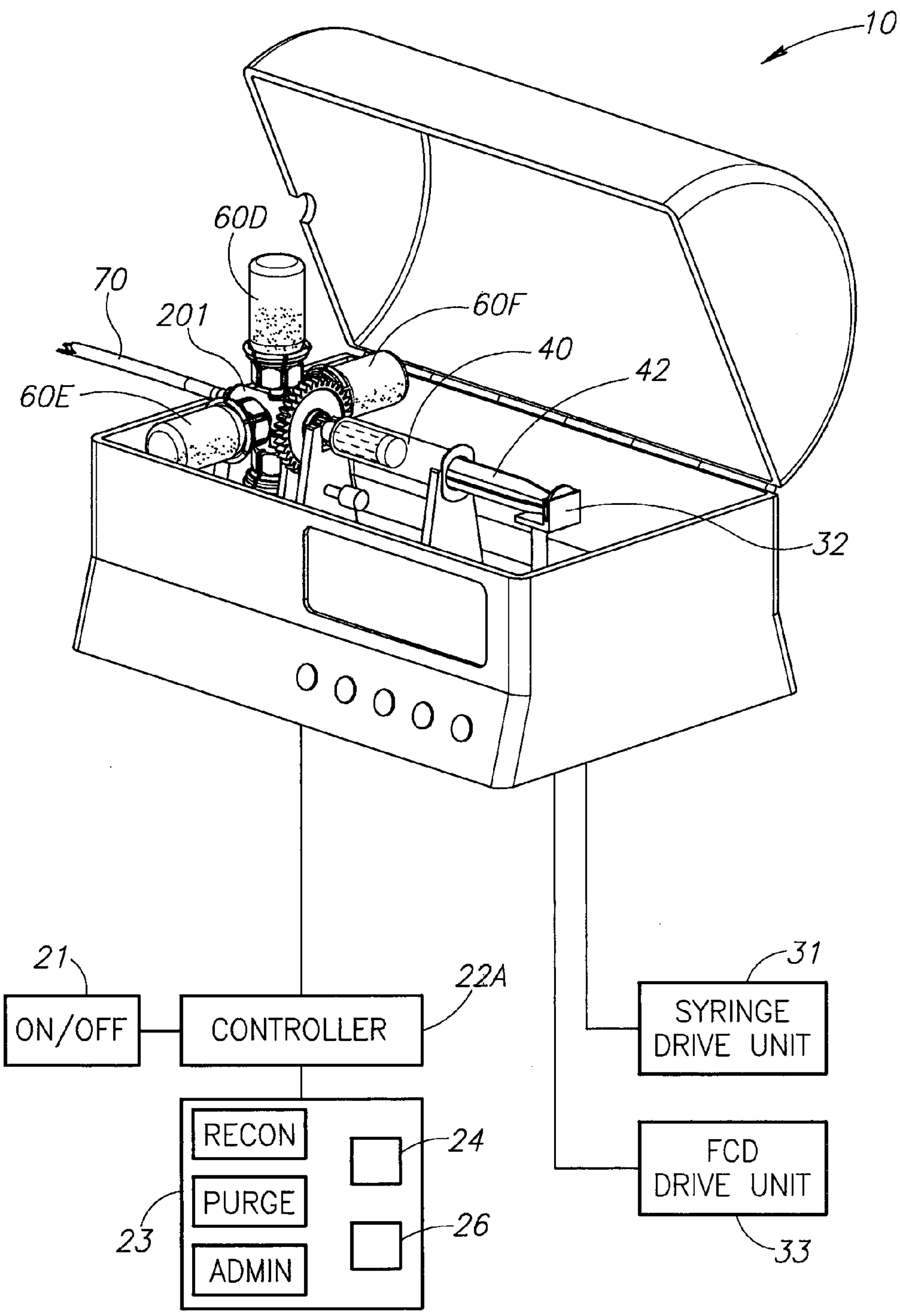
FIG. 17 shows a front perspective view of FIG. 1's medical apparatus having an assembled four vial kit with its syringe's plunger in its most backward position.
Figure 18:
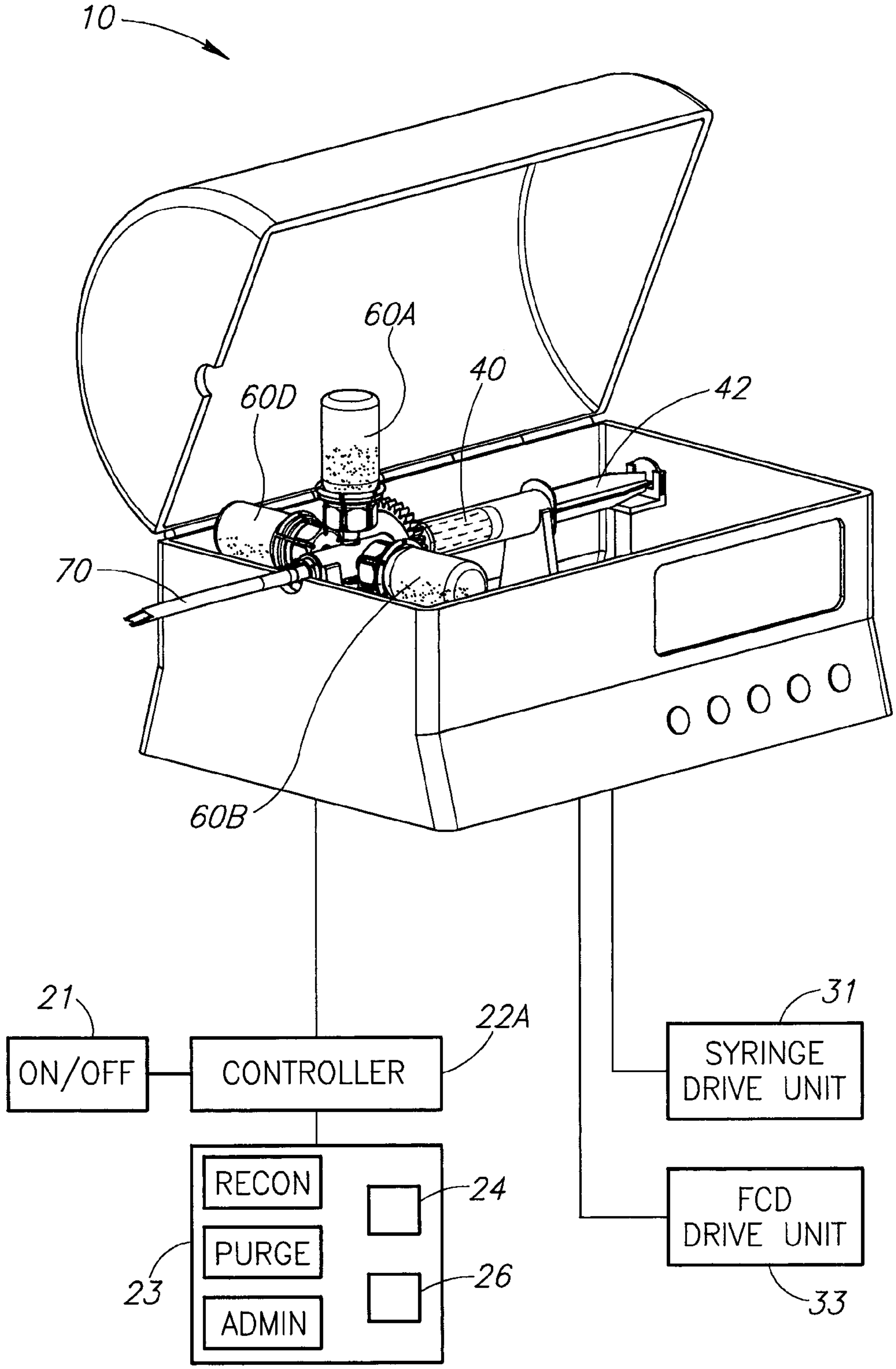
FIG. 18 shows a rear perspective view of FIG. 1's medical apparatus having an assembled four vial kit with its syringe's plunger in its most forward position.

FIGS. 17 and 18 show the two operative positions of the plunger head drive member 32 for fully depressing the plunger 42 to its most forward position for injecting liquid contents and fully withdrawing the plunger 42 to its most rearward position for aspirating liquid contents.

The operation of the medical apparatus 10 with a programmable controller 22B and a four vial kit 200 including a flow control device 201, an empty syringe 40, four vial adapters 50, a diluent containing vial 60D and three medicament containing vials 60E, 60F and 60G is similar to the aforesaid operation of the medical apparatus 10 with a pre-programmed controller 22A and the three vial kit 100. The major differences are as follows:

1. The kit 200 is supplied with the flow control device 201 in its FCP 21 ready for aspiration of the vial contents in flow communication with the first vial port 218
2. User is required to program the vial 60D's diluent volume
3. User is required to program the administration regime
4. User is required to attach the vial 60D to the first vial port 218 for the initial aspiration of its diluent contents prior to serial reconstitution of the remaining medicament contents of the remaining vials 60E, 60F and 60G.

Figure 19:
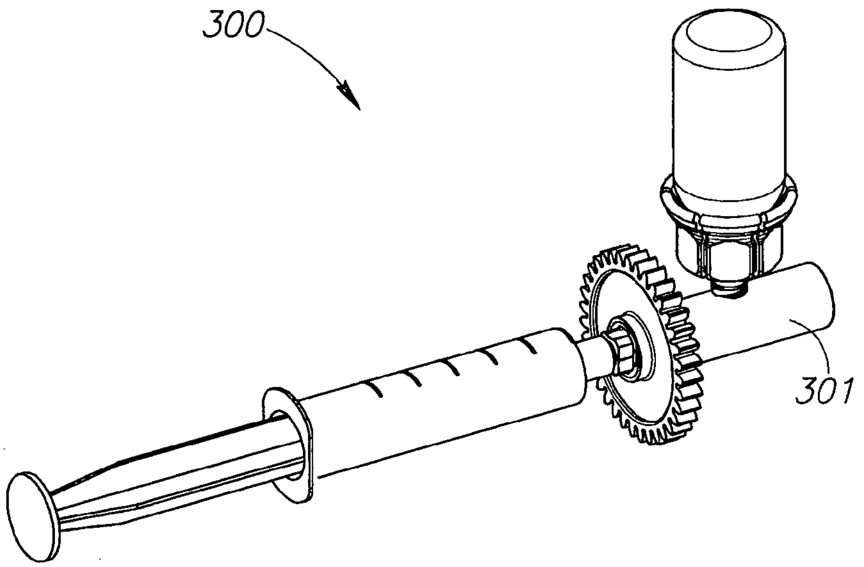
FIG. 19 shows a pictorial representation of an assemblage of a single use single vial kit including a single vial port flow control device, a syringe, a vial adapter, a vial and an administration line.
Figure 20:
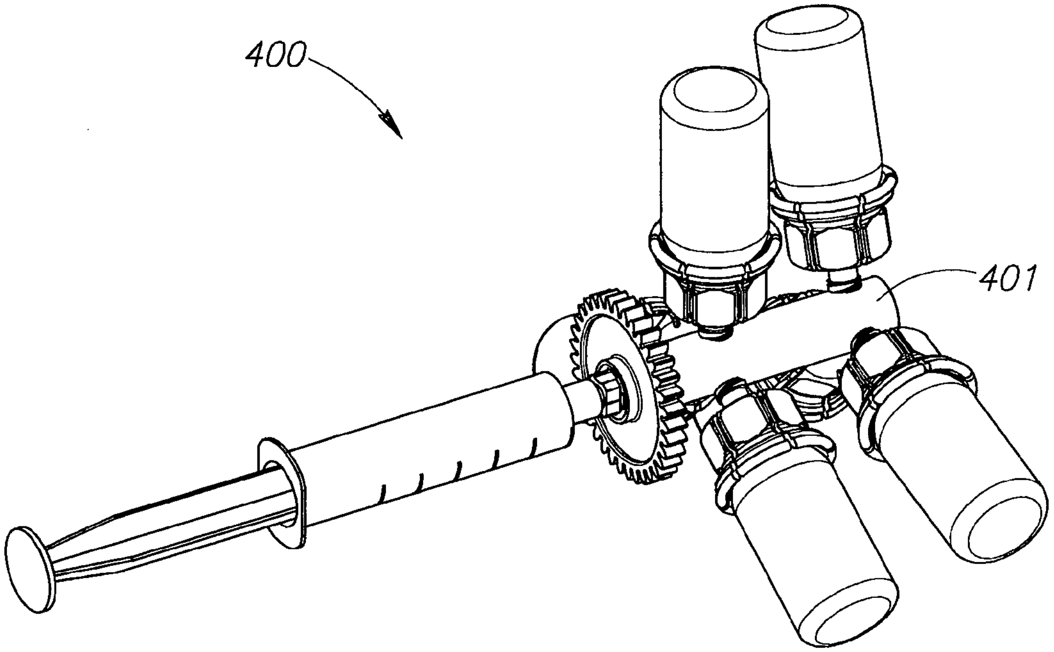
FIG. 20 shows a pictorial representation of an assemblage of a single use six vial kit including a six vial port flow control device, a syringe, six vial adapters, six vials and an administration line.

FIGS. 19 and 20 show two pictorial representations of assemblage of single use kits 300 and 400 including a single vial port flow control device 301 and a six vial port flow control device 401, respectively. The construction and operation of the flow control devices 301 and 401 are similar to the flow control devices 101 and 201 and are suitably adapted for their respective number of vial ports. The fluid control device 401 includes two sets of three peripheral equispaced vial ports disposed along its length.

Figure 21:
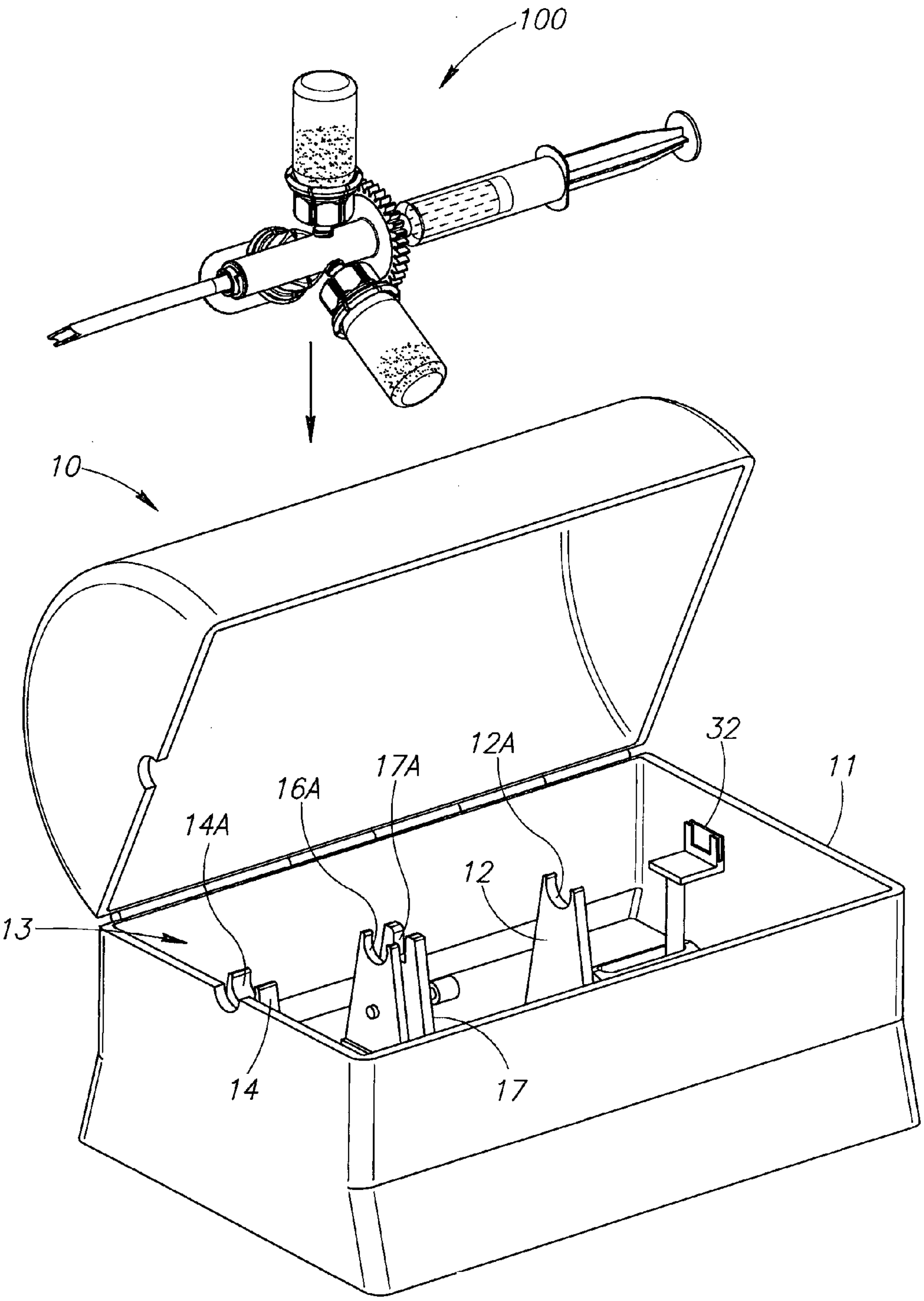
FIG. 21 shows a front perspective view of manual operated medical apparatus for reconstituting and administrating liquid drug dosages.

FIG. 21 shows medical apparatus 10 intended for manual operation with the three vial kit 100. The medical apparatus 10 includes a housing 11 having a syringe support 12 for horizontally supporting a syringe and a flow control device support 13 for horizontally supporting a flow control device.

While the invention has been described with respect to a limited number of embodiments, it will be appreciated that many variations, modifications, and other applications of the invention can be made within the scope of the appended claims.

The invention claimed is:

1. A flow control device for use with a syringe and at least one vial for reconstituting and administering a liquid drug dosage, the syringe having a reciprocal plunger with a proximal plunger head, the flow control device having a horizontal longitudinal axis and comprising:

(a) a stationary core member co-directional with the longitudinal axis and having an inlet port co-directional with the longitudinal axis for sealing fluid connection with the syringe and a pair of radial directed lumens perpendicular to the longitudinal axis and in flow communication with said inlet port, said pair of radial directed lumens including a downward radial directed injection lumen for injecting liquid contents into a vial in flow communication therewith and an upward radial directed aspiration lumen for aspirating liquid contents from a vial in flow communication therewith; and (b) an outer tubular flow control member co-directional with the longitudinal axis, rotatably mounted on and at least partially radially surrounding said core member, and having at least one peripheral located vial port for sealed attachment of a vial thereto and an administration flow channel in flow communication with an outlet port for administrating the liquid drug dosage, the at least one vial port being positioned in a plane oriented perpendicular to the longitudinal axis, the flow control device being operative such that said inlet port is in flow communication with a single port of said at least one vial port and said outlet port at each flow control position of at least two predetermined flow control positions of said flow control member relative to said core member for initially establishing a liquid drug reconstitution flow path between the syringe and each vial of the at least one vial for enabling initial reconstitution of the liquid drug dosage according to a liquid drug reconstitution program and subsequently establishing a liquid drug administration flow path between the syringe and the outlet port for administration of the liquid drug dosage according to a liquid drug administration regime, the flow control member being movable between the at least two predetermined flow control positions via rotation of the flow control member with respect to the core member about the longitudinal axis to align the single port of said at least one vial port and said outlet port at each flow control position with one of the radial directed lumens of the core member.

2. The device according to claim 1, wherein said flow control member includes a driven cogwheel for rotating said flow control member relative to said core member.

3. The device according to claim 1, wherein each vial port of said at least one vial port is integrally formed with a vial adapter for snap fit receiving a vial.

4. The device according to claim 1, wherein said flow control member includes a set of at least two peripheral located vial ports deployed at the same length therealong.

5. A kit for reconstituting and administrating a liquid drug dosage, the kit comprising a flow control device according to claim 1, a syringe and at least one vial.

6. Medical apparatus for reconstituting and administrating a liquid drug dosage, the medical apparatus intended for use with a flow control device according to claim 1, a syringe having a reciprocal plunger with a proximal plunger head, and at least one vial, the medical apparatus comprising a housing including a syringe support for horizontally supporting a syringe and a flow control device support for horizontally supporting a flow control device.

7. Medical apparatus according to claim 6 and further comprising a controller for controlling the operation of:

a motorized syringe drive unit for selectively reciprocating a plunger head drive member engaging the plunger head for reciprocating the plunger relative to the flow control device, and a motorized flow control device drive unit for selectively rotating the flow control member relative to the core member to a series of predetermined flow control positions for initially establishing a liquid drug reconstitution flow path between the syringe and each vial of the at least one vial for enabling initial reconstitution of the liquid drug dosage according to a liquid drug reconstitution program and subsequently establishing a liquid drug administration flow path between the syringe and the outlet port for administration of the liquid drug dosage according to a liquid drug administration regime.

8. Medical apparatus according to claim 7 wherein said controller reciprocates the flow control member back and forth relative to the core member for agitating a vial for reconstituting its powder contents.

9. Medical apparatus according to claim 7 wherein said controller is programmable for enabling manual input of said liquid drug reconstitution program.

10. Medical apparatus according to claim 7 wherein said controller is programmable for enabling manual input of said liquid drug administration regime.

* * * * *